(12) United States Patent
Neumann et al.

(10) Patent No.: US 10,733,910 B2
(45) Date of Patent: Aug. 4, 2020

(54) SYSTEMS AND METHODS FOR ESTIMATING PHYSIOLOGICAL HEART MEASUREMENTS FROM MEDICAL IMAGES AND CLINICAL DATA

(71) Applicant: Siemens Healthcare GmbH, Erlangen (DE)

(72) Inventors: Dominik Neumann, Erlangen (DE); Tommaso Mansi, Plainsboro, NJ (US); Sasa Grbic, Princeton, NJ (US); Bogdan Georgescu, Plainsboro, NJ (US); Ali Kamen, Skillman, NJ (US); Dorin Comaniciu, Princeton Junction, NJ (US); Ingmar Voigt, Erlangen (DE)

(73) Assignee: Siemens Healthcare GmbH, Erlangen (DE)

( * ) Notice: Subject to any disclaimer, the term of this patent is extended or adjusted under 35 U.S.C. 154(b) by 1135 days.

(21) Appl. No.: 14/915,478

(22) PCT Filed: Aug. 28, 2014

(86) PCT No.: PCT/US2014/053086
§ 371 (c)(1),
(2) Date: Feb. 29, 2016

(87) PCT Pub. No.: WO2015/031576
PCT Pub. Date: Mar. 5, 2015

(65) Prior Publication Data
US 2016/0210435 A1    Jul. 21, 2016

Related U.S. Application Data

(60) Provisional application No. 61/882,764, filed on Sep. 26, 2013, provisional application No. 61/870,849, filed on Aug. 28, 2013.

(51) Int. Cl.
*G09B 23/28* (2006.01)
*G16H 50/50* (2018.01)
(Continued)

(52) U.S. Cl.
CPC .......... *G09B 23/288* (2013.01); *G16H 50/50* (2018.01); *A61B 5/0044* (2013.01); *A61B 5/02* (2013.01);
(Continued)

(58) Field of Classification Search
CPC .... G06F 19/321; G16H 50/50; G09B 23/288; A61B 5/0044; A61B 5/02; A61B 5/04;
(Continued)

(56) References Cited

U.S. PATENT DOCUMENTS 7,651,466 B2    1/2010   Hatib et al.
8,774,906 B2    7/2014   Harks et al.
(Continued)

FOREIGN PATENT DOCUMENTS

CN    102421356    4/2012
JP    4896125 B2    3/2012

OTHER PUBLICATIONS

Sermesant et al, "Toward Patient-Specific Myocardial Models of the Heart", Elsevier, p. 289-301, 2008 (Year: 2008).*
(Continued)

*Primary Examiner* — Kamini S Shah
*Assistant Examiner* — Faraj Ayoub

(57) ABSTRACT

A method and system for estimating physiological heart measurements from medical images and clinical data disclosed. A patient-specific anatomical model of the heart is generated from medical image data of the patient. A patient-specific multi-physics computational heart model is generated based on the patient-specific anatomical model by personalizing parameters of a cardiac electrophysiology
(Continued)

model, a cardiac biomechanics model, and a cardiac hemodynamics model based on medical image data and clinical measurements of the patient. Cardiac function of the patient is simulated using the patient-specific multi-physics computational heart model. The parameters can be personalized by inverse problem algorithms based on forward model simulations or the parameters can be personalized using a machine-learning based statistical model.

45 Claims, 13 Drawing Sheets

(51) Int. Cl.
  A61B 5/00    (2006.01)
  G06N 5/00    (2006.01)
  A61B 5/04    (2006.01)
  A61B 5/02    (2006.01)
  A61B 8/08    (2006.01)
  A61B 5/055   (2006.01)
(52) U.S. Cl.
  CPC ............... *A61B 5/04* (2013.01); *A61B 5/055* (2013.01); *A61B 8/0883* (2013.01); *A61B 2576/023* (2013.01); *G06N 5/003* (2013.01)
(58) Field of Classification Search
  CPC . A61B 5/055; A61B 8/0883; A61B 2576/023; G06N 5/003
  USPC ............................................................. 703/2
  See application file for complete search history.

(56) References Cited

U.S. PATENT DOCUMENTS

| | | | |
|---|---|---|---|
| 9,129,053 B2 | 9/2015 | Mansi et al. | |
| 2008/0287812 A1* | 11/2008 | Parlikar | A61B 5/02007 600/485 |
| 2011/0060576 A1* | 3/2011 | Sharma | G06T 7/0012 703/11 |
| 2012/0022843 A1* | 1/2012 | Ionasec | G06T 13/20 703/9 |
| 2013/0197881 A1 | 8/2013 | Comaniciu et al. | |
| 2013/0197884 A1 | 8/2013 | Comaniciu et al. | |
| 2014/0207005 A1* | 7/2014 | Bukkapatnam | A61B 5/7235 600/485 |

OTHER PUBLICATIONS

Dolatabadi et al, "A simple model for ECG simulation from pairs of action potentials, normal subject", University of Western Ontario, 2010 (Year: 2010).*
Augenstein et al, "Method and apparatus for soft tissue material parameter estimation using tissue tagged magnetic resonance imaging", ResearchGate, p. 148-157, 2005 (Year: 2005).*
Korean Office Action dated Jul. 28, 2017 in corresponding Korean Application No. 2016-7008156.
Chinese Office Action dated Jul. 3, 2017 in corresponding Chinese application No. 201480047428.X(PCT/US2014/053086).
Sermesant, M. et al; "Patient-Specific Electromechanical Models of the Heart for the Prediction of Pacing Acute Effects in CRT: A Preliminary Clinical Validation;" Medical Image Analysis, Oxford University Press, Oxford, GB, vol. 16, No. 1 XP028124532 / Jul. 11, 2011.
Mansi, et al; "Data-Driven Computational Models of Heart Anatomy, Mechanics and Hemodynamics: An Integrated Framework," Biomedical Imaging (ISBI), 2012 9th IEEE Int'l. Symposium, p. 1434, XP032199297 / May 2, 2012.
Aguado-Sierra, et al; "Patient-Specific Modeling of Dyssynchronous Heart Failure: A Case Study," Progress in Biophysics and Molecular Biology, vol. 107, No. 1, pp. 147-155, XP028309-862 / Jul. 7, 2011.
Marchesseau, S. et al.: "Preliminary specificity study of the Bestel-Clement-Sorine electromechanical model of the heart using parameter calibration from medical images"; J Mech Behav Biomed Mater; vol. 20, pp. 259-271; 2013.
Sermesant, M et al: "Patient-specific electromechanical models of the heart for the prediction of pacing acute effects in CRT: A preliminary clinical validation" Medical Image Analysis,Oxford University Press,Oxford GB, vol. 16 No. 1, Jul. 11, 2011 (Jul. 11, 2011), pp. 201-215.
Relan, J., et al, "Coupled Personalization of Cardiac Electrophysiology Models for Prediction of Ischaemic Ventricular Tachycardia", Journal of the Royal Society Interface Focus vol. 1 No. 3, pp. 396-407, 2011.
Kanik, et al., "Estimation of Patient-Specific Material Properties of the Mitral Valve Using 40 Transesophageal Echocardiography," in Proceedings of International Symposium on Biomedical Imaging, 2013.
Konukoglu Ender et al. "Efficient probabilistic model personalization integrating uncertainty on data and parameters: Application to Eikonal-Diffusion models in cardiac electrophysiology" Progress in Biopbysics and Molecular Biology 107 (2011) 134-146.
Rapaka, et al., "LBM-EP: Lattice-boltzmann method for fast cardiac electrophysiology simulation from 3d images", In: Medical Image Computing and Computer-Assisted Intervention MICCAI, 2012, pp. 33-40, vol. 7511, Springer Berlin Heidelberg.
Mosegaard, et al., "A GPU accelerated spring mass system for surgical simulation," Studies Health Tech. & Inf., vol. 111, pp. 342-348, 2005.
Zettinig, et al., "From medical images to fast computational models of heart electromechanics: an integrated framework towards clinical use." International Conference on Functional Imaging and Modeling of the Heart. Springer, Berlin, Heidelberg, 2013.
Chabiniok, et al., "Estimation of tissue contractility from cardiac cine-MRI using a biomechanical heart model." Biomechanics and modeling in mechanobiology 11.5 (2012): 609-630.
Shi, et al., "Stochastic finite element framework for simultaneous estimation of cardiac kinematic functions and material parameters," Medical Image Analysis, vol. 7, pp. 445-464, 2003.
Delingette, et al., "Personalization of cardiac motion and contractility from images using variational data assimilation." IEEE transactions on biomedical engineering 59.1 (2012): 20-24.
Chinchapatnam, et al., "Model-based imaging of cardiac apparent conductivity and local conduction velocity for diagnosis and planning of therapy." IEEE Transactions on Medical Imaging 27.11 (2008): 1631-1642.
Folgoc, et al., "Current-based 4D shape analysis for the mechanical personalization of heart models." International MICCAI Workshop on Medical Computer Vision. Springer, Berlin, Heidelberg, 2012.
Zettinig, et al., "Fast Data-Driven Calibration of a Cardiac Electrophysiology Model from Images and ECG," in International Conference on Medical Image Computing and Computer-Assisted Intervention, Nagoya, 2013.
Zheng, et al., "Four-chamber heart modeling and automatic segmentation for 3-D cardiac CT volumes using marginal space learning and steerable features," IEEE Transactions on Medical Imaging, vol. 27, pp. 1668-1681, 2008.
Mitchell et al., "A Two-Current Model for the Dynamics of Cardiac Membrane", Bulletin of Mathematical Biology, 65(5):767-793, 2003.
Sermesant, et al.;, "An electromechanical model of the heart for image analysis and simulation," IEEE Transactions an Medical Imaging, vol. 25, No. 5, pp. 612-625, 2006.
Holzapfel, et al., "Constitutive modelling of passive myocardium: a structurally based framework for material characterization." Philosophical Transactions of the Royal Society A: Mathematical, Physical and Engineering Sciences 367.1902 (2009): 3445-3475.
Zaharescu, et al., "Surface feature detection and description with applications to mesh matching." 2009 IEEE conference on Computer Vision and Pattern Recognition. IEEE, 2009.

(56) References Cited

OTHER PUBLICATIONS

Le Folgoc, et al., "Current-based 4D shape analysis for the mechanical personalization of heart models." International MICCAI Workshop on Medical Computer Vision. Springer, Berlin, Heidelberg, 2012.
Peyrat, et al., "Registration of 4D cardiac CT sequences under trajectory constraints with multichannel diffeomorphic demons." IEEE Transactions on Medical Imaging 29.7 (2010): 1351-1368.
Perperidis, et al., "Spatio-temporal free-form registration of cardiac MR image sequences." Medical image analysis 9.5 (2005): 441-456.
Powell, "The NEWUOA software for unconstrained optimization without derivatives." Large-scale nonlinear optimization. Springer, Boston, MA, 2006. 255-297.
Shimodaira, "Improving predictive inference under covariate shift by weighting the log-likelihood function." Journal of statistical planning and inference 90.2 (2000): 227-244.
Pan, et al, "A Survey on Transfer Learning," IEEE Transactions on Knowledge and Data Engineering, vol. 22, No. 10, pp. 1345-1359, 2010.
Eldred, Michael S., et al. Dakota, a multilevel parallel object-oriented framework for design optimization, parameter estimation, uncertainty quantification, and sensitivity analysis. Tech. Rep. SAND2006-6337, Sandia National Laboratories, 2006.
Clayton, et al., "Models of cardiac tissue electrophysiology: progress, challenges and open questions." Progress in biophysics and molecular biology 104.1-3 (2011): 22-48.

\* cited by examiner

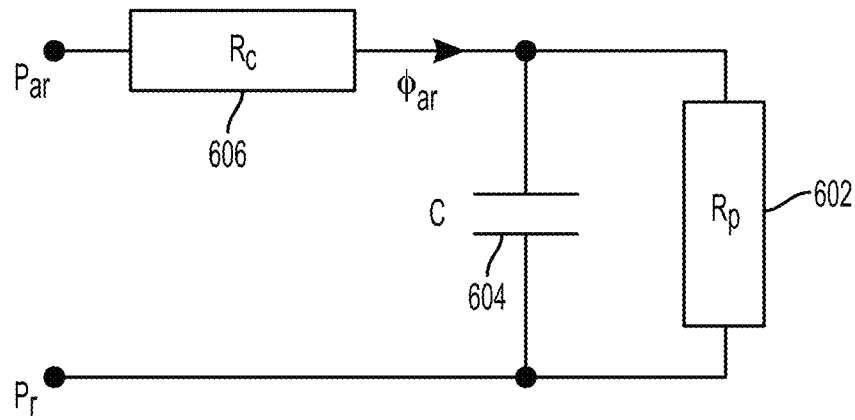

FIG. 6

| ALGORITHM 1 EP PERSONALIZATION WORKFLOW |
|---|
| 700 → REQUIRE: INITIAL $T_{Cl}^0$ AND DIFFUSIVITY $C_M^0, C_L^0, C_R^0$ |
| 701 → 1: $T_{Cl}^1 = T_{Cl}^0 + \Delta QT,m - calcQT(T_{Cl}^0, C_M^0, C_L^0, C_R^0)$ |
| 702 → 2: $K^* = \text{argmin}_K (\Delta QRS,m - calcQRS(T_{Cl}^1, K(C_M^0, C_L^0, C_R^0)))$ |
| 703 → 3: $(C_M^*, C_L^1, C_R^1) = K^* (C_M^0, C_L^0, C_R^0)$ |
| 704 → 4: $C_L^*, C_R^* = \text{argmin}C_L, C_R (\alpha_m - calcEA(T_{Cl}^1, C_M^*, C_L, C_R))$ |
| 705 → 5: $T_{Cl}^* = T_{Cl}^1 + \Delta QT,m - calcQT(T_{Cl}^1, C_M^*, C_L^*, C_R^*)$ |
| 706 → 6: RETURN PERSONALIZED EP PARAMETERS $T_{Cl}^*, C_M^*, C_L^*,$ AND $C_R^*$ |

FIG. 7

ALGORITHM 2 MECHANICS PERSONALIZATION WORKFLOW (LV)

800 → REQUIRE: INITIAL $\sigma^0, E^0$ AND $p_{PV}^0$

801 → 1: $p_{PV}^* = p_{PV}^0 + \min p_m - \min \text{calcPr}(\sigma^0, E^0, p_{PV}^0)$ 802 → 2: $\sigma^*, E^* = \text{argmin}_{\sigma,E} \xi((p_m, v_m), \text{calcPrVol}(\sigma, E, p_{PV}^*))$ 803 → 3: RETURN PERSONALIZED PARAMETERS $\sigma^*, E^*, p_{PV}^*$

SYSTEMS AND METHODS FOR ESTIMATING PHYSIOLOGICAL HEART MEASUREMENTS FROM MEDICAL IMAGES AND CLINICAL DATA

This application claims the benefit of U.S. Provisional Application No. 61/870,849, filed Aug. 28, 2013, and U.S. Provisional Application No. 61/882,764, filed Sep. 26, 2013, the disclosures of which are herein incorporated by reference in their entirety.

BACKGROUND OF THE INVENTION

The present invention relates to estimating physiological heart measurements of a patient based on medical image data and clinical measurements, and more particularly, to estimating physiological heart measurements to personalize a multi-physics heart model for a patient for disease diagnosis and therapy planning.

Heart failure, a common form of cardiovascular disease with significant mortality and morbidity rates, is a major threat to public health. Its causes are manifold and challenging to diagnose or treat. Accordingly, complex heart models capable of simulating cardiac function in order to provide more information from clinical data, calculate new risk scores or to predict therapy outcomes are desirable.

BRIEF SUMMARY OF THE INVENTION

The present invention provides methods and systems for estimating physiological heart measurements from medical images and clinical data in order to personalize a multi-physics heart model. Embodiments of the present invention provide comprehensive frameworks for full cardiac electromechanics personalization from routinely acquired medical imaging and clinical data. Embodiments of the present invention allow for fast generation of reproducible patient-specific computational models of the heart.

In one embodiment of the present invention, A patient-specific multi-physics computational heart model is generated based on the patient-specific anatomical model by personalizing parameters of a cardiac electrophysiology model, a cardiac biomechanics model, and a cardiac hemodynamics model using a marginal approach based on medical image data and clinical measurements of the patient, wherein the parameters for at least one of the cardiac electrophysiology model, the cardiac biomechanics model, or the cardiac hemodynamics model are personalized using a regression model trained on a database of training samples based on features extracted from the medical image data and clinical measurements of the patient. Cardiac function of the patient is computed using the patient-specific multi-physics computational heart model. The cardiac model is visualized through moving meshes and the estimated parameters are returned to a user.

These and other advantages of the invention will be apparent to those of ordinary skill in the art by reference to the following detailed description and the accompanying drawings.

BRIEF DESCRIPTION OF THE DRAWINGS

FIG. 6 illustrates a 3-element Windkessel model;

FIG. 7 illustrates an algorithm for personalizing the cardiac electrophysiology (EP) model according to an embodiment of the present invention;

DETAILED DESCRIPTION

The present invention relates to estimating physiological heart measurements from medical images and clinical data in order to personalize a multi-physics heart model for patient. Embodiments of the present invention are described herein to give a visual understanding of the methods for personalizing a computational multi-physics heart model. A digital image is often composed of digital representations of one or more objects (or shapes). The digital representation of an object is often described herein in terms of identifying and manipulating the objects. Such manipulations are virtual manipulations accomplished in the memory or other circuitry/hardware of a computer system. Accordingly, is to be understood that embodiments of the present invention may be performed within a computer system using data stored within the computer system.

Figure 1:
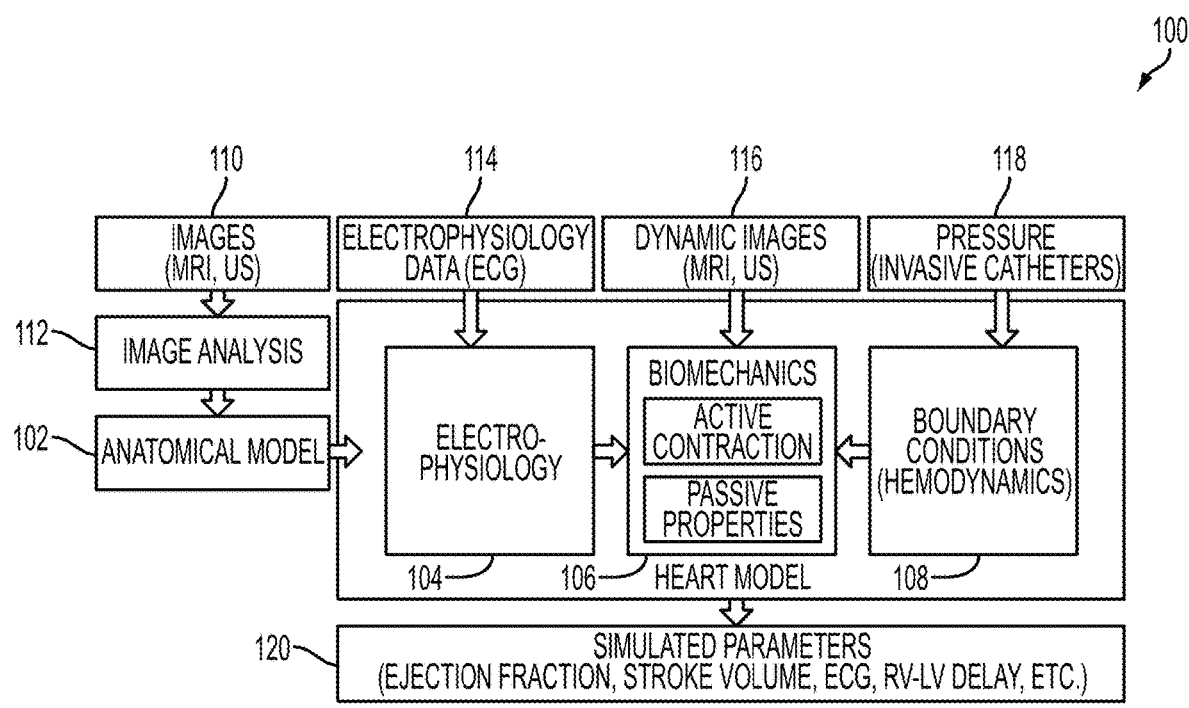
FIG. 1 illustrates a computational multi-physics heart model according to an embodiment of the present invention.

FIG. 1 illustrates a computational multi-physics heart model according to an embodiment of the present invention. The multi-physics heart model 100 provides complete model of heart electromechanics. As shown in FIG. 1, the main components of the multi-physics heart model 100 include an anatomical model 102, a cardiac electrophysiology model 104, a cardiac biomechanics model 106, and a cardiac hemodynamics model 108. Once the cardiac electrophysiology model 104, the cardiac biomechanics model 106, and the cardiac hemodynamics model 108 are personalized for a patient, the patient-specific multi-physics heart model 100 is used to simulate cardiac function of the patient in order to calculate simulated parameters 120, such as ejection fraction, stroke volume, ECG, RV-LV delay, etc. Additional details regarding the multi-physics heart model are described in U.S. Published Patent Application No. 2013/0197881 and U.S. Published Patent Application No. 2013/0197884, the disclosures of which are incorporated here by reference.

The anatomical model 102 is a model of patient-specific heart morphology obtained from volumetric image data 110 (e.g., MRI, CT, DynaCT, 3D ultrasound) using automated image analysis 112. According to an advantageous implementation, a robust, data-driven machine learning approach is used to automatically estimate triangulated meshes of the endocardia and the epicardium. Appending both meshes yields a closed surface of the biventricular myocardium. The closed contour at end-diastasis is finally transformed into a tetrahedral volume using a mesh generation algorithm. Next, myocardium fibers are mapped to the patient-specific anatomical model. Two options can be used to map the myocardium fibers to the patient-specific anatomical model. In a first option, the fiber architecture is computed on the patient-specific morphology using a rule-based system, in which below the basal plane, fiber elevation angles vary linearly from epicardium (−70°) to endocardium (+70°), and geodesic distances on the mesh are used to extrapolate the angles up to the valves. It is to be understood that the angles listed above are exemplary values, which can be adapted by a user. In a second option, for patients where diffusion tensor imaging (DTI) is available, the fiber architecture provided by the DTI is mapped directly to the patient-specific anatomical model.

The cardiac electrophysiology model 104 calculates cardiac electrophysiology, which is computed over the whole cardiac cycle using the patient-specific anatomical model 102. In order to achieve realistic results and high computational performance, the Mitchell-Schaeffer mono-domain electrophysiology model can be employed and the electrophysiology model can be solved using the Lattice-Boltzmann method for electrophysiology (LBM-EP). According to an advantageous implementation, the electrophysiology model can be coupled with an electrocardiogram model. The cardiac electrophysiology model 104 can be personalized for a patient based on electrophysiology data 114, such as an electrocardiogram (ECG), of the patient. It should be noted that the present invention is not limited to a particular electrophysiology model and in various implementations, the Mitchell-Schaeffer model can be replaced by other cellular models of electrophysiology.

The cardiac biomechanics model 106 simulates deformation of the patient-specific anatomical model 102 by solving the dynamics equation $M\ddot{u}+C\dot{u}+Ku=F_a+F_p+F_b$, where $\ddot{u}$, $\dot{u}$ and $u$ gather accelerations, velocities and displacements of the mesh nodes, and M, K and C are the mass matrix, internal elastic stiffness matrix and Rayleigh damping matrix, respectively. $F_a$, $F_p$ and $F_b$ model active stress, ventricular pressure, and mechanical boundary conditions, respectively. The active forces $F_a$ can be computed by a model that expresses the active Cauchy stress tensor in terms of an action potential. This model is mainly governed by three parameters, namely the maximum contraction that can be reached by a cell and the ATP binding and release rates. The model simplifies the true myocyte contraction and thus only approximates the behavior of the complex underlying bio-physical phenomena. However, this allows for the number of parameters to be rather low while clinically observable, enabling robust personalization of the model. More advanced models could similarly be employed without significant modification. The passive stress $F_p$ can be computed using linear models or orthotropic models, such as the orthotropic Holzapfel-Ogden (H-O) model [20]. The H—O model is derived from considerations of the myocardial tissue structure, meaning that cardiac tissue shows different behavior whether it is stretched along the fiber direction, perpendicular to the fiber, etc. The H—O model comprises eight material constants, which are contained within an exponential stress-strain energy function. Reformulating the energy using multiplicative Jacobian energy decomposition (MJED) allows for efficient computation of patient-specific tissue biomechanics. Both the effect of arteries and atria on ventricular motion and a pericardium constraint are considered within the biomechanical model as mechanical boundary conditions, which account for the force vectors $F_b$. The cardiac biomechanics model 106 can be personalized based on dynamic image data 116, such as 4D MRI, CT, or ultrasound of a patient.

The cardiac hemodynamics model 108 is a lumped model of cardiac hemodynamics, which mimics the blood flow in the four cardiac phases. This is achieved by alternating endocardial boundary conditions. During filling and ejection, atrial and arterial pressure is applied directly using the nodal forces $F_p$ from the dynamics equation described above. In between, i.e. during isovolumetric contraction and isovolumetric relaxation, an isovolumetric constraint based on an efficient projection-prediction method or a penalty constraint is enabled in order to keep the ventricular volume constant. Arterial and atrial pressures can be calculated using a Windkessel and elastance model respectively. Pressure measurements 118 of the patient can be used to personalize the cardiac hemodynamics model 108. The pressure measurements 108 may be wire pressure measurements acquired via an invasive catheter procedure or cuff pressure measurements.

Figure 2:
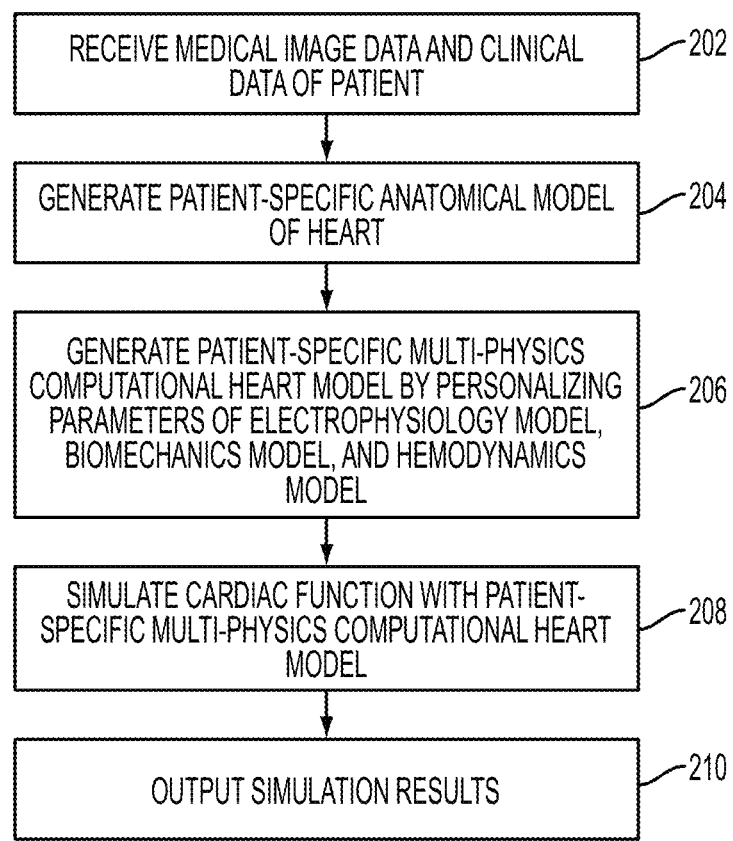
FIG. 2 illustrates a method of simulating cardiac function using a patient-specific computational multi-physics heart model according to an embodiment of the present invention.

FIG. 2 illustrates a method of simulating cardiac function using a patient-specific computational multi-physics heart model according to an embodiment of the present invention. The method of FIG. 2 transforms medical image data and clinical measurements of a patient to generate a patient-specific computational multi-physics heart model and then simulates cardiac function of the patient using the patient-specific computational multi-physics heart model. Referring to FIG. 2, at step 202, medical image data and clinical data of the patient are received. The medical image data can be 3D medical images including a cardiac region of the patient. The medical images may be a dynamic sequence of medical images acquired over at least one complete heart cycle. In advantageous embodiments of the present invention, the medical images can be MRI images, CT images, DynaCT, and/or ultrasound images, but the present invention is not necessarily limited to these imaging modalities. The medical images may be received directly from a medical imaging device, such as an MR, CT, or ultrasound scanner, or the medical images may be received by loading stored medical images of a patient. The clinical data can include non-imaging patient-specific measurements, such as ECG, arterial and ventricular pressure measurements, etc. The ECG may be a 12-lead ECG acquired from the patient. The pressure measurements may be acquired by catheter-based invasive pressure measurements or cuff pressure measurements.

Figure 3:
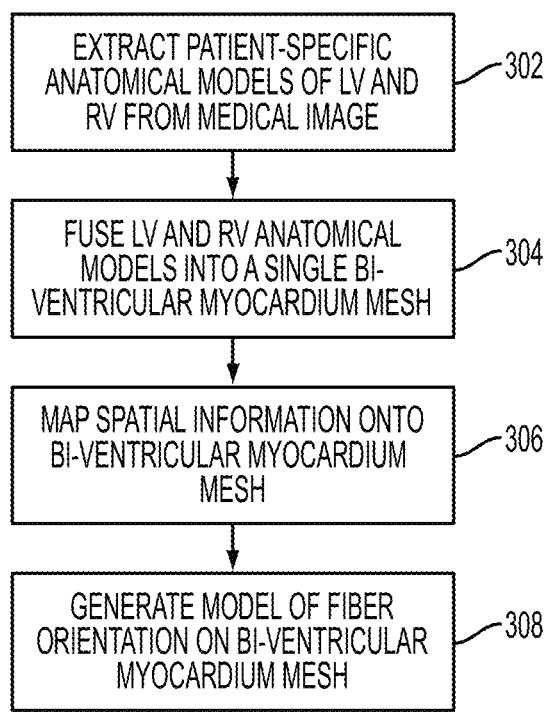
FIG. 3 illustrates a method for generating the patient-specific anatomical model of the left and right ventricles according to an embodiment of the present invention.

At step 204, a patient-specific anatomical model of the heart is generated from on the medical image data of the patient. The patient-specific anatomical model can include all of the cardiac chambers or a subset of the cardiac chambers. According to an advantageous implementation, the patient-specific anatomical model can include the left ventricle (LV) and the right ventricle (RV). FIG. 3 illustrates a method for generating the patient-specific anatomical model of the left and right ventricles according to an embodiment of the present invention. The method of FIG. 3 can be used to implement step 204 of FIG. 2. At step 302, anatomical models of the LV and RV are extracted from the medical images. In an advantageous embodiment, the LV and RV anatomical models show patient-specific heart morphology and dynamics, and are calculated automatically from MRI or ultrasound images. The LV and RV models can be detected in any preoperative images (e.g., US or cardiac MR) that cover the entirety of both cardiac ventricles. The LV and RV models can be extracted by segmenting the left endocardium, right endocardium, epicardium, and left and right outflow tract using a marginal space-learning based machine learning method. Obtained triangulations (meshes) are automatically labeled according to the anatomy they represent for subsequent processing.

For each of the LV and the RV, the heart chamber segmentation can be formulated as a two-step learning problem: anatomical structure localization and boundary delineation. In an advantageous embodiment, marginal space learning (MSL) can be used to apply machine learning to 3D object detection. The idea of MSL is not to learn a monolithic classifier directly in the full similarity transformation parameter space but to incrementally learn classifiers on marginal spaces. In particular, the detection of each heart chamber can be split into three problems: position estimation, position-orientation estimation, and position-orientation-scale estimation. A separate classifier is trained based on annotated training data for each of these estimation problems. The classifiers in the lower dimensional marginal spaces are used to prune the searching space efficiently. This object localization stage results in an estimated transformation (position, orientation, and scale) of the object (e.g., heart chamber).

After automatic object localization, the mean shape model of the object is aligned with the estimated transformation to get a rough estimate of the object shape. The shape is then deformed locally to fit the object boundary. Active shape models (ASM) can be used to deform an initial estimate of a non-rigid shape under the guidance of the image evidence and the shape prior. However, a non-learning based generic boundary detector, as used in conventional ASM applications, does not work effectively in heart chamber deformation due to the complex background and weak edges. Instead, a learning based boundary detector can be used to exploit more image evidences to achieve robust boundary detection. Additional details regarding MSL-based heart chamber segmentation are described in U.S. Pat. No. 7,916,919, issued Mar. 29, 2011, and entitled "System and Method for Segmenting Chambers of a Heart in a Three Dimensional Image", United States Published Patent Application No. 2010/0040272, and United States Published Patent Application No. 2012/0022843, which are incorporated herein by reference.

At step 304, the patient-specific LV and RV models are fused into a single bi-ventricular myocardium volumetric mesh. In a possible implementation, the LV and RV anatomies extracted can be fused together. The resulting closed surface is used to create a volumetric, tetrahedral mesh on which vertices are tagged into surface zones according to the underlying anatomy.

At step 306, spatial information is mapped onto the bi-ventricular myocardium mesh. Spatial information, such as scars, grey zones, and fibrosis can be identified in images, such as late delayed-enhancement MR images and mapped onto the bi-ventricular myocardium mesh. For example, scar locations and extent can be segmented in delayed-enhancement MR images. The scar information is mapped onto the bi-ventricular myocardium mesh by tagging the tetrahedral elements that lie within the segmented scar regions. This spatial information is important to simulate the electrical wave around scars, in particular for wave-reentry assessment, but also the impaired contractility due to dead tissue.

At step 308, model of fiber orientation is generated on the bi-ventricular myocardium mesh. In one embodiment, in-vivo diffusion tensor (DT) MR images of the patient's cardiac fibers are directly mapped to the anatomical model through image registration. In this case, the DT MR image is non-linearly registered to the medical image in which the LV and RV models are detected. The resulting transformation is used to deform the tensor field in the DT MR image towards the anatomical model. The Finite Strain method, the details of which are described in Peyrat et al., "A Computational Framework for the Statistical Analysis of Cardiac Diffusion Tensors: Application to a Small Database of Canine Hearts", *IEEE TMI,* 26(11):1500-1514, 2007, which is incorporated herein by reference, is used to reorient the tensors once the tensors are registered to the anatomical model.

In another embodiment, if no in-vivo DT MR images are available, the model of fiber orientation may be computed directly from the anatomical model using a rule-based method. A generic model of myocardium fiber architecture that includes fiber and fiber sheets is computed. A rule-based strategy is followed to generate the fiber architecture to cover the entire bi-ventricular myocardium from apex to valves. Below the basal plane, which is identified automatically using point correspondences of the initial triangulations of the anatomical model, the fiber elevation angle α, i.e. their angle with respect to the short axis plane, varies linearly across the myocardium, from −70° on the epicardium to +70° on the endocardium. Similarly, the sheet direction, which is defined by the angle β with respect to the outward transmural axis, varies linearly across the myocardium, from +45° on the epicardium to −45° on the endocardium. α and β are computed for each point of the volumetric bi-ventricular myocardium mesh between the apex and basal plane based on the geodesic distance to the endocardia and epicardia identified by the facet tags: $\alpha = (d_{ept} \alpha_{endo} + d_{endo} \alpha_{ept})/(d_{endo} + d_{ept})$, where $d_{ept}$, $d_{endo}$, $\alpha_{ept}$, and $\alpha_{endo}$ are the distances and angles at the endocardium and epicardium, respectively. The fiber and sheet orientations are then fixed around each valve. In particular, fibers are longitudinal around the aortic valve and tangential around the mitral, tricuspid, and pulmonary valves, and sheet normals are oriented towards the barycenter of the valves. The local orthonormal basis is then interpolated from the basal plane to the valve, first by following the myocardium surface, then throughout the myocardium wall. For orthonormality preservation, the interpolation can be performed using a Log-Euclidean framework.

Figure 4:
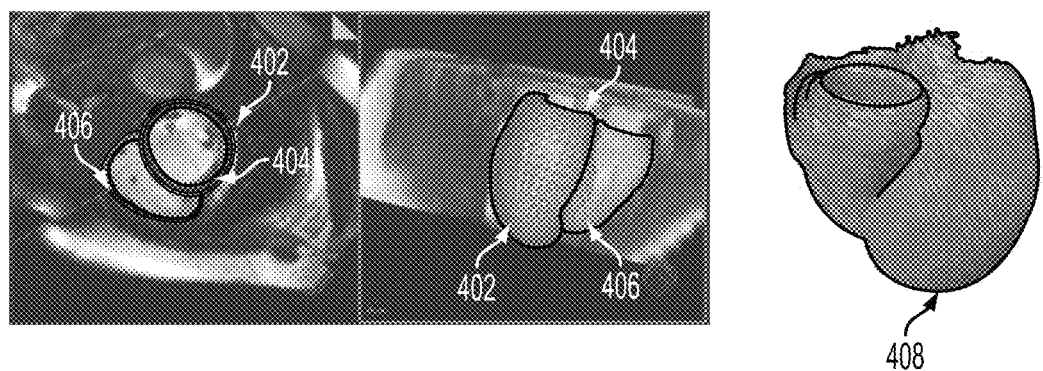
FIG. 4 illustrates exemplary results for generating patient-specific anatomical model.

FIG. 4 illustrates exemplary results for generating patient-specific anatomical model. In particular, FIG. 4 shows segmented meshes for the LV endocardium 402, LV epicardium 404, and RV 406 overlaid on an MR image, and a generated volumetric fiber model 408.

Returning to FIG. 2, at step 206, a patient-specific multi-physics computational heart model is generated for the patient by personalizing parameters of the electrophysiology model, the biomechanics model, and the hemodynamics model. In an advantageous implementation, 17 total parameters are personalized: 5 each for Windkessel models of both arteries for the hemodynamics model; myocardial, left (LV) and right (RV) ventricular diffusivity, and time during which the ion channels are closed for the electrophysiology (EP) model; and Young's modulus and LV and RV myocyte contraction for tissue biomechanics.

At step 208, cardiac function of the patient is simulated using the patient-specific multi-physics computational heart model. The simulation can be used to estimate simulated parameters, such as ejection fraction, stroke volume, ECG, RV-LV delay, etc. The simulation can also be used to simulate various therapies, such as cardiac resynchronization therapy, ablation, etc. At step 210, the simulation results are output.

Figure 5:
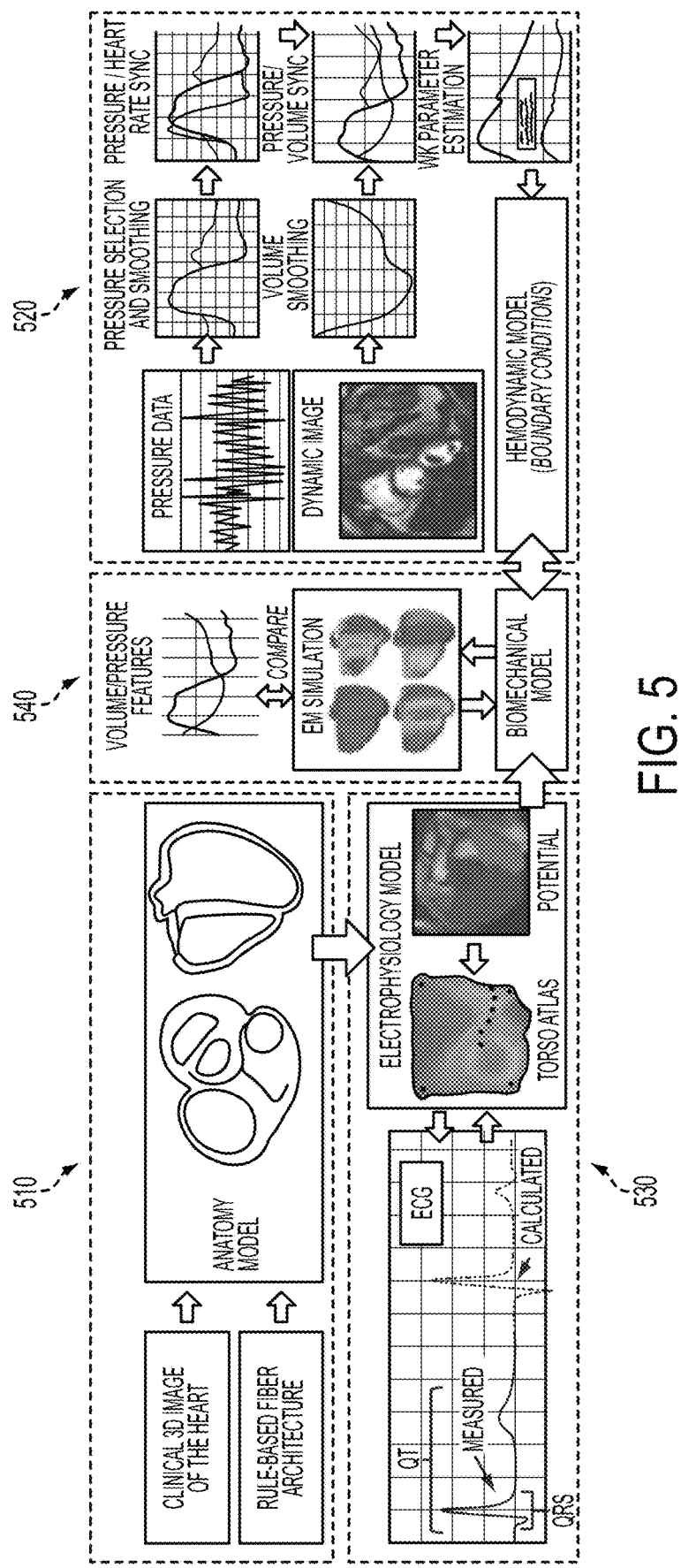
FIG. 5 illustrates a method for personalizing the parameters of the patient-specific multi-physics computational model according to an embodiment of the present invention.

In a first embodiment of the present invention, the patient-specific multi-physics computational model is personalized (step 206 of FIG. 2) by solving for parameters of the forward model for each model component (hemodynamics, EP, and biomechanics) directly based on the medical image data and/or clinical data of the patient using inverse problem algorithms. FIG. 5 illustrates a method for personalizing the parameters of the patient-specific multi-physics computational model according to an embodiment of the present invention. The method illustrated in FIG. 5 utilizes inverse problem algorithms to personalize parameters of the cardiac hemodynamics model, the cardiac EP model, and the cardiac biomechanics model. Referring to FIG. 5, at step 510, the patient-specific anatomical model is generated using robust machine learning and mesh processing based on a clinical 3D image of the heart and a rule-based fiber architecture. The details of generating the patient-specific anatomical model are described above in the description of step 204 of FIG. 2 and the method of FIG. 3.

At step 520, the cardiac hemodynamics model is personalized based on pressure measurements and dynamic medical images of the patient. A lumped model of cardiac hemodynamics is employed, which mimics the four cardiac phases by alternating endocardial boundary conditions. During filling and ejection, atrial and arterial pressure is applied directly, while in between (isovolumetric contraction and relaxation), an isovolumetric constraint based on an efficient projection-prediction method is enabled to keep the ventricular volume constant. Arterial pressures are calculated using a 3-element Windkessel (WK) model and atrial pressures are calculated using an elastance model.

The hemodynamics personalization estimates the WK parameters of artery compliance, characteristic and peripheral resistance, remote pressure, and initial pressure, for both coronary arteries. The hemodynamics personalization relies on the arterial pressure measured during cardiac catheterization and a blood pool volume curve derived from 4D medical image data (e.g., MRI). The blood pool volume curve can be generated based on the patient-specific anatomical model by estimating the blood pool volume at each time point based on the volume of the segmented ventricles in a corresponding frame of the 4D cardiac image data. In a possible implementation, the method for measuring left ventricle volume described in U.S. Pat. No. 8,098,918, which is incorporated herein by reference, can be used to calculate the blood pool volume in each frame. This results in volume curve with an estimated volume for each of a plurality of time points over at least one cardiac cycle. The temporal derivative of the volume curve provides the ventricular blood flow (negative during systole and positive during diastole) at each time point. The arterial inflow is equal to the opposite ventricular flow during systole, assuming no regurgitation. Accordingly, the arterial inflow can be calculated at each time point based on the temporal derivative of the blood pool volume.

In order to personalize the cardiac hemodynamics model, a cardiac cycle is interactively selected from the pressure trace. The arterial and ventricular pressure is low-pass filtered, resulting in a smoothed pressure curve. The blood pool volume curve is also low-pass filtered. Next, the pressure curve is automatically adjusted to match the heart rate at the 4D medical image data acquisition so that the pressure curve will be synchronized with the arterial inflow estimate obtained from the medical image data. As simple temporal scaling would not be physiologically coherent, a rule-based algorithm is applied to adjust the pressure curve. First, the systolic portion of the pressure curve is stretched such that the ejection time observed on the pressure curve is equal to the ejection time measured on the volume curve. The ejection time on the pressure curve is the time during which the ventricular pressure is higher than or equal to the arterial pressure. The ejection time on the blood pool volume curve is the time during which the ventricular flow is negative. As described above, the ventricular blood flow is the temporal derivative of the blood pool volume. Accordingly, the ejection time on the blood pool volume curve is the time during which the derivative or slope of the volume curve is negative. The pressure curve is then shifted to synchronize the pressure curve with the cardiac cycle of the blood pool volume curve. Once the systolic portion of the pressure curve is stretched such that the ejection time of the pressure curve is equal to the ejection time of the volume curve, the remaining portion of the pressure curve can be adjusted such that the total time for the cardiac cycle is equal to the total time of the cardiac cycle in the volume curve. The pressure curve is then shifted so that it is aligned in time with the blood pool volume curve.

Once the pressure curve is adjusted to be synchronized with the blood pool volume curve, the parameters of the WK model are estimated. FIG. 6 illustrates a 3-element Windkessel model. As shown in FIG. 6, the first element of the model is a peripheral resistance $R_p$ 602, which accounts for the distal resistance of the circulatory system mainly due to the small vessels. The compliance C 604 accounts for the elasticity of the arterial walls, whereas the characteristic resistance $R_c$ 606 accounts for the blood mass and for the compliance of the artery proximal to the valves. These parameters ($R_p$, C, and $R_c$) are estimated based on the synchronized pressure curve and arterial inflow estimate. Let $\Phi_{ar}(t)$ be the arterial inflow at time t, defined as the opposite of the ventricular flow, $p_{ar}(t)$ be the arterial pressure at time t, and $p_r$ be a constant low pressure of reference (typically the pressure of the remote venous system). $p_r$ is typically set to be between 0 and 5 mmHg and in a possible implementation $p_r=0$. When blood flows into the arteries ($\Phi_{ar}(t)>0$) during ejection, the 3-element Windkessel model can be expressed as:

$$\frac{dp_{ar}(t)}{dt} = R_c \frac{d\Phi_{ar}(t)}{dt} + \left(1 + \frac{R_c}{R_p}\right)\frac{\Phi_{ar}(t)}{C} - \frac{p_{ar}(t) - p_r}{R_p C}$$

When the valves are closed, the blood flow is stopped ($\Phi_{ar}(t)=0$), and the 3-element Windkessel model can be expressed as:

$$\frac{dp_{ar}(t)}{dt} = -\frac{p_{ar}(t) - p_r}{R_p C}$$

These equations can be integrated using first (or higher) order implicit or stable explicit schemes.

Once the pressure curve is synchronized with the volume curve, and thus the arterial inflow estimate, the Windkessel model is used to calculate pressure for a plurality of time steps based on the arterial inflow estimate at each time step. The calculated pressure values are compared to the pressure values of the synchronized pressure curve and the parameters of the Windkessel model ($R_p$, $C$, and $R_c$) are estimated automatically using an optimization procedure, which minimizes a cost function. The parameters of the Windkessel model can be initialized with preset default values, such as mean population wide arterial resistance and compliance values. According to an advantageous embodiment, the cost function used optimize the Windkessel parameters is:

$$\min_{R_c, R_p, C, p_0} \left\{ \frac{1}{N} \sum_{i=1}^{N} (p_m[i] - p_c[i])^2 + \dot{u}_{min}^2 + \dot{u}_{max}^2 \right\}$$

where $p_m$ and $p_c$ are vectors containing the time-sequence of measured and computed arterial pressure, respectively, $p_0$ is an initial arterial pressure value for the Windkessel model, N is a number of pressure samples, and $\dot{u}_{min}$ and $\dot{u}_{max}$ are penalty terms ($\min(p_m) - \min(p_C)$) and ($\max(p_m) - \max(p_C)$), respectively. According to a possible implementation, the simplex method can be used to minimize the cost function and estimate the optimal Windkessel parameters. For increased robustness, the cost function is duplicated over N cycles and the forward model calculated for all of these cycles. The cost function is evaluated only at the latest cycle. The simplex method is used to estimate all of the parameters but the initial pressure $p_0$. The initial pressure $p_0$ is obtained automatically from the computed pressure curve over several cycles, such that the first computed pressure cycle is close to steady state.

Returning to FIG. 5, at step 530, the cardiac electrophysiology (EP) model is personalized based on a measured ECG of the patient. Cardiac EP models ranging from simplified Eikonal models to highly detailed ionic models are available. According to an advantageous implementation, the Mitchell-Schaeffer (MS) phenomenological model, which has parameters closely related to the shape of the action potential, is used as the cardiac EP model and is solved using LBM-EP, a near real-time solver for patient-specific cardiac EP based on an efficient GPU implementation of the Lattice-Boltzmann method. The LBM-EP algorithm is described in greater detail in U.S. Published Patent Application No. 2013/0226542, entitled "Method and System for Fast Patient-Specific Cardiac Electrophysiology Simulations for Therapy Planning and Guidance," and U.S. Published Patent Application No. 2014/0022250, entitled "System and Method for Patient Specific Planning and Guidance of Ablative Procedures for Cardiac Arrhythmias," which are incorporated herein by reference in their entirety. The main free parameters that need to be personalized in order to generate realistic EP for the patient include tissue diffusivity c, which determines the speed of electrical wave propagation throughout the heart, and the time during which ion channels are closed $\hat{o}_{cl}$. The fast regional diffusivity for the left $c_L$ and right $c_R$ endocardia are modeled to mimic the Purkinje network, and a slower diffusivity $c_M \leq c_L$, $c_M \leq c_R$ is modeled for the myocardium.

According to an advantageous embodiment, this EP personalization framework is useable without the need for specialized data such as contact mapping catheters. Hence, the EP parameters can be estimated solely based on routinely acquired 12-lead ECG data of the patient. In order to calculate ECG signals from the simulated EP, the anatomical heart model is registered to a torso atlas, a mapping of the simulated potentials on the anatomical model to the torso is then calculated, and ECG signals are calculated based on the potentials at pre-defined torso lead positions.

FIG. 7 illustrates an algorithm for personalizing the cardiac EP model according to an embodiment of the present invention. Let calcQT, calcQRS, and calcEA be procedures which run an EP simulation on a patient-specific anatomical model using the provided parameters and then calculate the named ECG feature (QT, QRS, and electrical axis (EA), respectively) by mapping the simulated potentials to the torso, as described above. Automatic methods are used to derive the duration of the QRS and QT complex ($\Delta_{QRS}$ and $\Delta_{QT}$, respectively), and electrical axis (á) from the lead signals calculated from the simulated EP. $\Delta_{QRS,m}$, $\Delta_{QT,m}$, and $\alpha_m$ are measured values extracted from the clinical ECG images of the patient. Referring to FIG. 7, at 700, the parameters are initialized as $\hat{o}_{cl}^0$, $c_M^0$, $c_L^0$, and $c_R^0$. For example, standard values from literature can be used for the initialization. At 701, an updated value $\hat{o}_{cl}^1$ is calculated based on the initial value $\hat{o}_{cl}^0$, the measured QT duration ($\Delta_{QT,m}$), and the calculated QT resulting from an EP simulation using the initial parameters $\hat{o}_{cl}^0$, $c_M^0$, $c_L^0$, and $c_R^0$. At 702, an optimization is performed to find an optimal value k* that minimizes a cost function that compares the measured QRS duration ($\Delta_{QRS,m}$) with the calculated QRS resulting from an EP simulation using parameters of the updated value $\hat{o}_{cl}^1$ and k($c_M^0$, $c_L^0$, $c_R^0$). At 703, the personalized value of $c_m$* is set and updated values $c_L^1$, and $c_R^1$ are calculated based on the optimal value of k*. At 704, personalized values of $c_L$* and $c_R$* are determined by performing an optimization to find values of $c_L$ and $c_R$ that minimize a cost function that compares the measured electrical axis ($\alpha_m$) with the calculated electrical axis resulting from an EP simulation using the parameters of ($\hat{0}_{cl}^1$, $c_M$* $c_L$, $c_R$). At 705, a personalized value of $\hat{o}_{cl}$* is calculated based on the updated value $\hat{o}_{cl}^1$, the measured QT duration ($\Delta_{QT,m}$), and the calculated QT resulting from an EP simulation using the updated parameter $\hat{o}_{cl}^1$, and the personalized parameters $c_M$*, $c_L$*, and $c_R$*. At 706, the personalized EP parameters $\hat{o}_{cl}$*, $c_M$*, $c_L$*, and $c_R$* are output. The optimization steps of 702 and 704 can be performed using a robust gradient-free optimization technique, such as NEWUOA.

Returning to FIG. 5, at step 540, the cardiac biomechanics model is personalized. The EP signal is coupled with myocardial tissue mechanics through models of active and passive tissue behavior to compute realistic cardiac motion. Accordingly, the dynamics equation $M\ddot{u} + C\dot{u} + Ku = f_a + f_p + f_b$ must be solved (e.g., using finite element methods). $\ddot{u}$, $\dot{u}$, and u denote accelerations, velocities, and displacements, respectively, of the mesh nodes, and M, K, and C are the mass internal elastic stiffness, and Rayleigh damping matrix, respectively. $f_a$, $f_p$, and $f_b$ model active stress, ventricular pressure, and boundary conditions, respectively.

According to an advantageous implementation, a phenomenological model is utilized for the active myocyte contraction, which is to a large extent governed by ó, the maximum asymptotic strength of the active contraction. The transverse isotropic linear elasticity can be relied on to model passive myocardial properties using co-rotational linear tetrahedra to cope with large deformations (mainly observed during systole). Young's modulus E, with respect to the fiber architecture, and Poisson ratio (e.g., í=0.48), a measure of tissue incompressibility, are the main parameters of the cardiac biomechanical model.

Figures 8, 9:
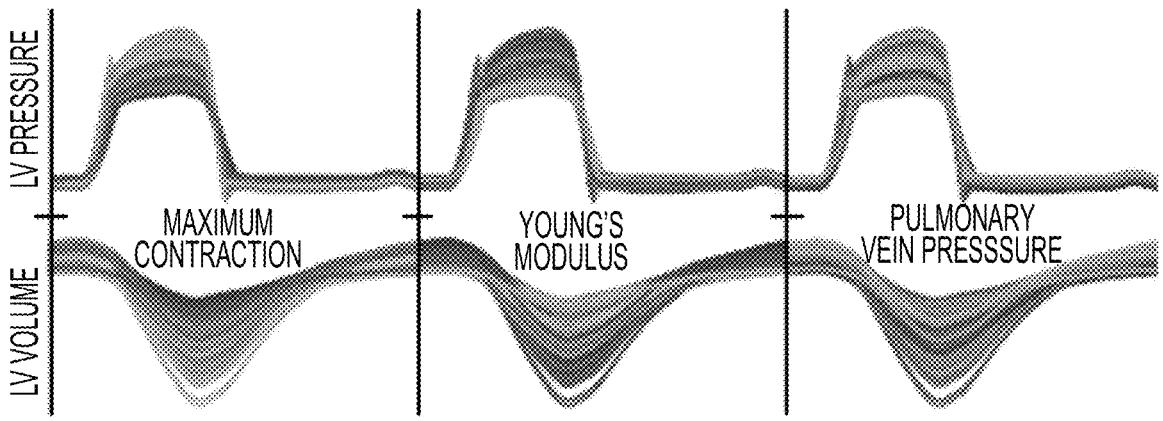
FIG. 8 illustrates an algorithm for personalizing the cardiac biomechanics model according to an embodiment of the present invention.
FIG. 9 illustrates exemplary results of a sensitivity analysis on passive and active biomechanical parameters.

FIG. 8 illustrates an algorithm for personalizing the cardiac biomechanics model according to an embodiment of the present invention. According to an advantageous implementation, ó is estimated independently for left and right ventricular mechanics. In the algorithm of FIG. 8, the procedures calcPr and calcPRVol return vectors containing time-sequences of pressure data and pressure and volume data, respectively, after running a forward simulation of the full electromechanical (EM) model given the provided parameters. The full EM model refers to the coupled cardiac EP and biomechanics and hemodynamics model. $p_{PV}$ denotes the pulmonary vein pressure. Referring to FIG. 8, at 800, the parameters of the maximum asymptotic strength of active contraction, Young's modulus, and pulmonary vein pressure are initialized as $ó^0$, $E^0$, and $p_{PV}^0$. For example, standard values from literature can be used for the initialization. At 801, the personalized pulmonary vein pressure $p_{PV}^*$ is determined based on the initial pulmonary vein pressure $p_{PV}^0$ and a difference between a minimum measured pressure value and a minimum calculated pressure value resulting from a full EM simulation using the initial parameters $ó^0$, $E^0$, and $p_{PV}^0$. At 802, personalized values of ó* and E* are determining by performing an optimization that finds the values of ó and E that minimize a cost function that compares measured and pressure and volume curves ($p_m$, $v_m$) and calculated volume resulting from a full EM simulation using the parameters of (ó, E, $p_{PV}^*$). The cost function $î=ë(å_{EF}, å_{SV}, å_{min\,v}, å_{max\,v}, å_{min\,p}, å_{max\,p})^T$ returns a value describing the similarity between measured pressure and volume curves ($p_m$, $v_m$) and calculated pressure and volume curves ($p_c$, $v_c$) by comparing a weighted sum of features including ejection fraction (EF), stroke volume (SV), minimum volume (min v), maximum volume (max v), minimum pressure (min p), and maximum pressure (max p), where $å_X=(X_m-X_c)^2$. In an advantageous implementation, ë is set to $ë=(1,10^{-4}, 10^{-4}, 10^{-4}, 10^{-4}, 10^{-4})$ to cope with distinct units. To minimize transient effects, two heart cycles can be simulated and the calculated values are derived from the second simulated heart cycle. Optimization of the cost function can be performed using a robust gradient-free optimization technique, such as NEWUOA. At 803, the personalized parameters of ó*, E*, and $p_{PV}$ are output.

Figure 10:
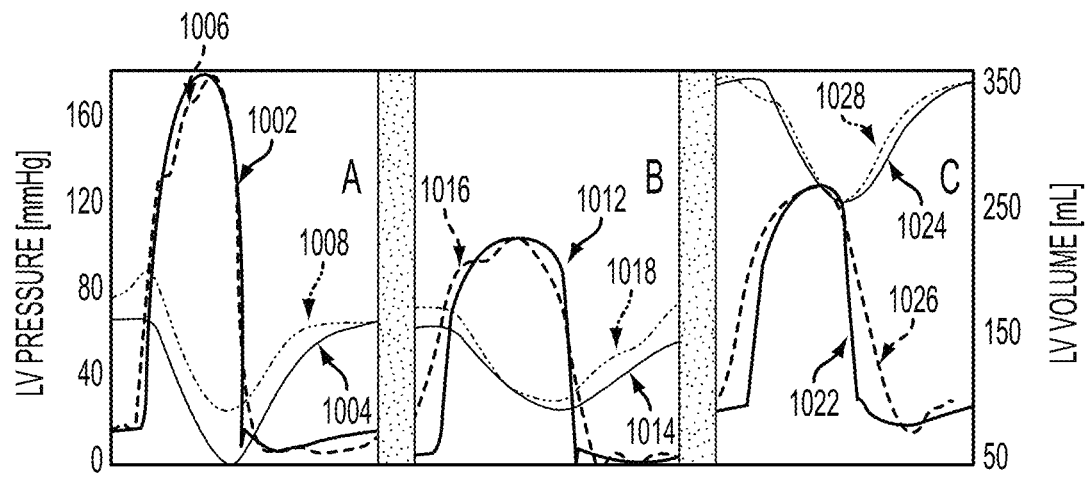
FIG. 10 illustrates exemplary pressure and volume curves after personalization of the patient-specific multi-physics model in three patients using the method of FIG. 5.

The present inventors tested the proposed personalization technique of FIG. 5 on patients with a large variety in phenotype. For example, the maximum LV pressure ranged from 78 mmHg to 177 mmHg, and measured LV EFs ranged from 10.5% to 59.8%. This makes personalization a particularly challenging task and thus, robust estimation techniques are essential. FIG. 9 illustrates exemplary results of a sensitivity analysis on passive and active biomechanical parameters. The results of sensitivity analysis depict variability in volume and pressure curves introduced by varying model input parameters. A clear trend is observable for the maximum contraction ó around the minimum volume and maximum pressure, implying that these two indicators are key features for predicting ó. Similar conclusions can be drawn for Young's modulus E and the pulmonary vein pressure $p_{PV}$. In addition, the sensitivity analysis reveals that maximum contraction ó and elasticity E are most crucial for changes in ventricular volume and pressure. Furthermore, pressure originating from the pulmonary vein $p_{PV}$ (LV) or vena cava (RV) dominates diastolic ventricular pressure. FIG. 10 illustrates exemplary pressure and volume curves after personalization of the patient-specific multi-physics model in three patients using the method of FIG. 5. As shown in FIG. 10, curves 1002, 1012, and 1022 are simulated pressure curves for patients A, B, and C, respectively. Curves 1004, 1014, and 1024 are simulated volume curves for patients A, B, and C, respectively. Curves 1006, 1016, and 1026 are measured pressure curves for patients A, B, and C, respectively. Curves 1008, 1018, and 1028 are measured volume curves for patients A, B, and C, respectively.

Due to the modular architecture of the pipeline of FIG. 5, embodiments of the present invention are not limited to a single model. For example, although the use of linear elasticity was described here, more sophisticated models of passive biomechanical properties, such as orthotropic models, can be used as well. This may allow for generating more realistic results in some cases.

In a second embodiment of the present invention, the patient-specific multi-physics computational model is personalized (step 206 of FIG. 2) using statistical machine-learning based techniques to directly estimate patient parameters from clinical observation based on the medical images and clinical data of the patient. Instead of using inverse problem algorithms to estimate the parameters based on a number of forward simulations, this embodiment utilizes a trained statistical model (e.g., regression function) learned from a database of training samples to estimate the parameters of the patient-specific multi-physics computational model from features extracted from the medical image data and clinical data of the patient.

Figure 11:
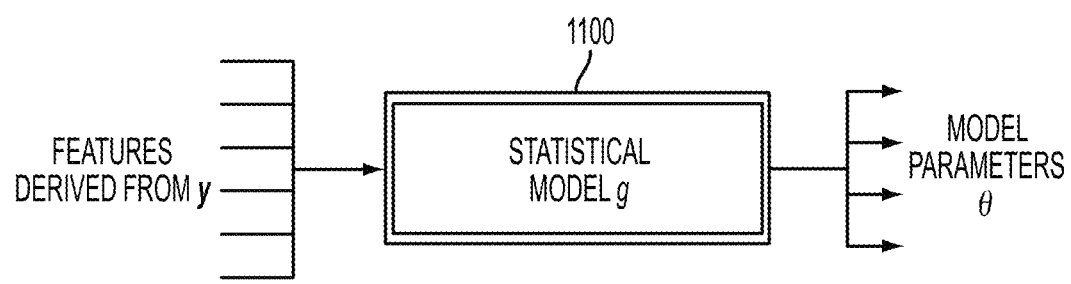
FIG. 11 illustrates a machine-learning based statistical model.

The forward model described in the embodiment of FIG. 5 can be seen as a dynamic system y=f(è), where the system output y is the dynamic anatomy (volumetric representation of the myocardium deformed over time), cardiac electrophysiology, electrocardiogram and hemodynamics parameters like pressure and valvular flow. $è=(è_a, è_e, è_b, è_h)$ is the full set of input parameters of the model, covering all components of the model: anatomy $è_a$, cardiac electrophysiology $è_e$, biomechanics $è_b$, and hemodynamics $è_h$. This embodiment of the present invention aims to solve the inverse problem $è=f^{-1}(y)$. This is achieved by using statistical learning techniques in order to learn a non-linear mapping $g(y) \approx f^{-1}(y)$ that approximates the inverse problem. FIG. 11 illustrates a machine-learning based statistical model. As shown in FIG. 11, the statistical model g 1100 is trained to estimate model parameters è of the cardiac multi-physics model from features derived from outputs y of the cardiac multi-physics model.

Figure 12:
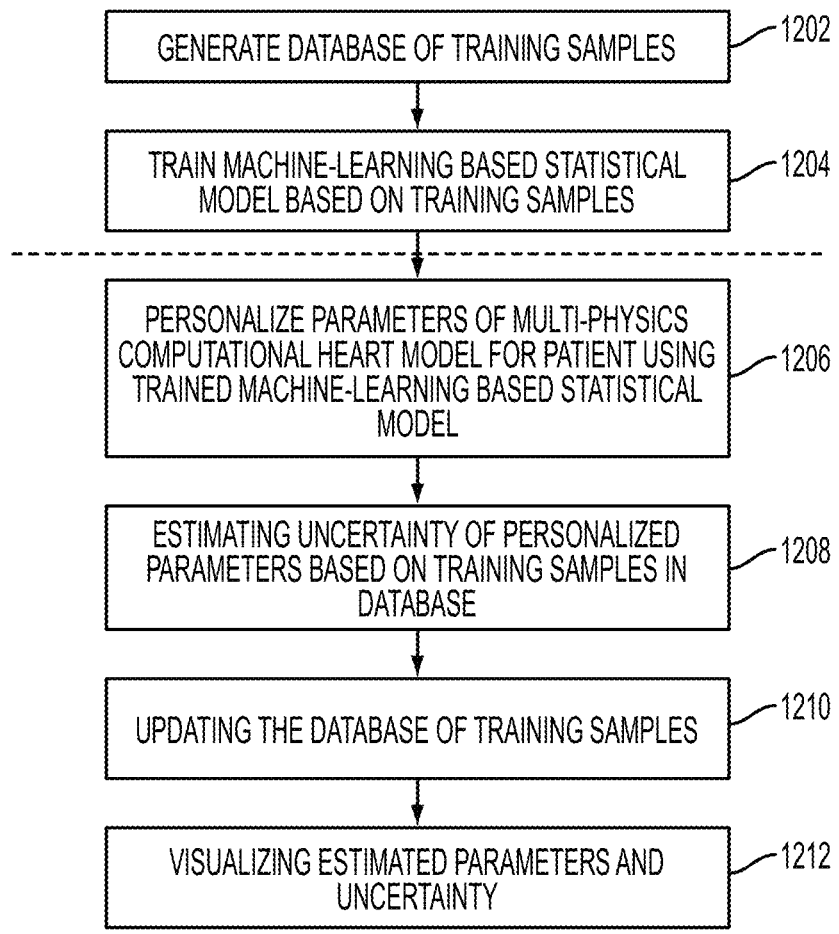
FIG. 12 illustrates a method for personalizing parameters of the computational multi-physics model using a trained statistical model according to an embodiment of the present invention.

FIG. 12 illustrates a method for personalizing parameters of the computational multi-physics model using a trained statistical model according to an embodiment of the present invention. Referring to FIG. 12, steps 1202 and 1204 are implemented offline in a training phase prior to using the on-line use of the trained learning-based statistical model to personalize parameters of a patient-specific multi-physics computational heart model.

At step 1202, a database of training samples is generated. The training samples can include a number of personalized electromechanical models for different patients, each including a known set of parameters and a known set of model outputs. Due to the fact that in many scenarios the number of available data from different patients may be too small to build a robust regression model for the large dimensionality of cardiac parameters, the forward model described above in connection with FIGS. 1 and 5 can be used to generate a large amount of training samples. For each available set of patient data, the workflow can be implemented as follows: First, the electromechanical model is calibrated with respect to the patient's clinical data, for example utilizing the parameter estimation method of FIG. 5 that was described above. Next, a range of possible values is defined for each of the parameters that will be estimated using the trained statistical model, yielding a subspace in the dim(è)-dimensional space of model parameters. This subspace is then sampled either on a uniform grid or using a statistical sampling method (in the simplest case: drawing samples from the uniform distribution defined by the subspace, or using more sophisticated techniques). For each parameter sample, a simulation is run using the forward model and the result is stored. Ideally, all parameters should be varied by this procedure, however, this may not be feasible from a computational point of view, since each simulation may take a considerable amount of time and the output produced by each simulation includes a temporal sequence of 3D representations of the patient's anatomy, which need to be stored digitally.

Utilizing this workflow, a large database DB={$(y_i, \varphi_i, è_i)|i=1 \ldots N$} of N simulations can be created where for all $i=1 \ldots N$ the ground-truth mapping is known for both the dynamic system f: $è_i \rightarrow y_i$ and for the inverse problem g: $y_i \rightarrow è_i$. $y_i$ is the temporal sequence of 3D models for the i-th simulation computed using the electromechanical model parameters $è_i$, electrophysiology parameters, electrocardiogram and hemodynamics variables. $\varphi_i$ is a vector of features computed from $y_i$.

At step 1204, a machine-learning based statistical model is trained based on the training samples. From the dynamic system's output y a set of physiologically-related features φ are extracted, which will be used to learn a regression model g during training and to estimate the model parameters during testing. It is important to note that these features are by construction observable from clinical data in order to be able to process unseen datasets. The features can be computed from simple geometrical measurements over time from the dynamic model (e.g. statistical features of temporal curves of, e.g., the volume of the left ventricle) or more sophisticated geometric, kinematic and temporal features. For cardiac electrophysiology, ECG features are also used in the estimation process. The list of features may include, but is not limited to: ejection fraction, stroke volume, left ventricle pressure (min, max, mean, std. dev.), left ventricle volume (min, max, mean, std. dev.), left atrium pressure (min, max, mean, std. dev.), left atrium volume (min, max, mean, std. dev.), artery pressure (min, max, mean, std. dev.), blood flow (min, max, mean, std. dev.), shape descriptors, cardiac dynamics descriptors, and electrophysiology descriptors (ECG, electrical axis, etc.).

To ensure comparability of feature values between different patients and heart rates, depending on the type of feature, temporal or spatio-temporal registration of the 4-dimensional (3D+t) volumetric representation of the heart (output of simulation or segmented sequence from temporal imaging data of a patient) may need to be performed before computing the feature values. Temporal misalignment can occur when there are differences in length of the cardiac cycles or when differences in other dynamic properties of the heart are present. Typically, one wants to match an event occurring at time t in the reference sequence to a similar event occurring at the corresponding time t' in the target sequence. In this case, the arising correspondence problem can be solved simply by comparing physiological states (e.g., end of diastole/systole or ECG-based measurements) in the target and reference sequence. For the computation of some of the features it is important to be careful regarding temporal and spatio-temporal registration, since the temporal signatures of abnormalities should not be removed. In this case, an option would be to only synchronize the heart rates. This can be achieved by first synchronizing the ejection times, and then synchronizing the diastasis. Therefore, only the volume curve and the pressure curve of the given datasets are required for this synchronization.

A regression model is trained based on all available simulations in the database DB. A grid-search can be used to adjust the parameters of the regression model to achieve optimal results. To assess the regression performance of a particular regression model, we quantify its accuracy using leave-one-patient-out cross-validation or similar validation techniques. In leave-one-patient-out cross validation, the regression model is learned using only simulations that do not stem from a particular patient, and tested using the simulations of the left-out patient to see whether the model generalizes well. Several statistical methods can be used to learn the regression model g and to associate features derived from y with the model parameters è of the multi-physics heart model, such as: Multivariate Regression Splines (MARS), Support Vector Machine Regression, Gradient Boosting Regression, Random Forest (Randomized Trees) Regression, and Multivariate Polynomial Regression. According to a possible implementation, a single regression model may be trained to estimate all of the parameters è of the multi-physics cardiac model. In another possible implementation, a separate regression model may be trained to estimate the parameters of each of the respective sub-models (cardiac electrophysiology, cardiac biomechanics, and cardiac hemodynamics) of the multi-physics heart model. In another possible implementation, a marginal space learning approach can be used to increase efficiency by training regression functions for one or more of the sub-models (cardiac electrophysiology, cardiac biomechanics, and cardiac hemodynamics) in a series of search spaces having increasing dimensionalities.

At step 1206, parameters of the multi-physics computational heart model are personalized for the patient using the trained learning-based statistical model. In particular, the features described above are extracted from the medical image data and the clinical measurements of the patient and the regression function g trained at step 1204 is used to estimate the model parameters based on the extracted features. According to a possible implementation, the patient-specific anatomical model is extracted prior to this personalization step (see step 204 of FIG. 2), and features are extracted from the dynamic patient-specific anatomical model. In a possible implementation, the trained regression model can estimate the entire set of model parameters for the multi-physics model. In another possible implementation a separate trained regression model can be used to estimate the parameters for each of the cardiac electrophysiology model, cardiac biomechanics model, and cardiac hemodynamics model. In another possible implementation, the parameters for one or more of the sub-models can be estimated using a trained regression function and parameters for one or more of the sub-models can be estimated based on forward simulations using the inverse problem techniques discussed above.

Figure 13:
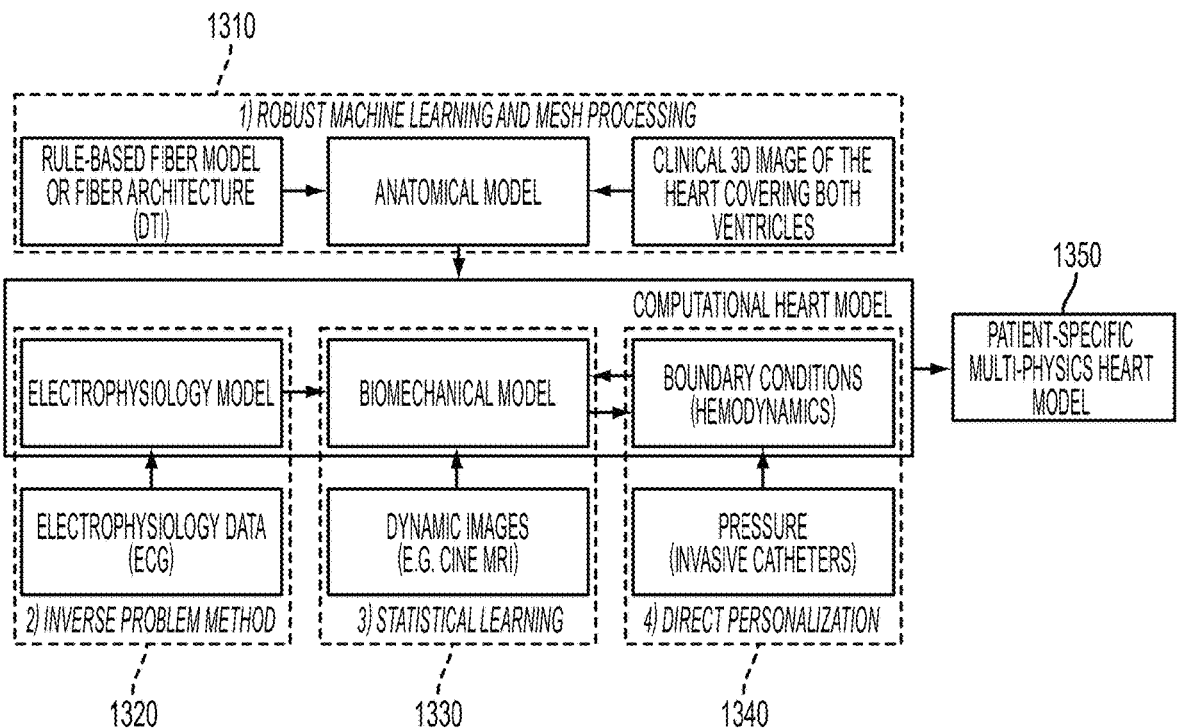
FIG. 13 illustrates a marginal space learning pipeline for personalizing parameters of the multi-physics heart model according to an embodiment of the present invention.

FIG. 13 illustrates a marginal space learning pipeline for personalizing parameters of the multi-physics heart model according to an embodiment of the present invention. Marginal in this context means that we will first do the anatomy, then the electrophysiology, then the hemodynamics, and finally the biomechanics. The process could be iterated to refine the estimates. In this way, the dimensionality of the problem is reduced and the machine learning approach is enabled. In order to personalize the entire set of electromechanical model parameters $\grave{e}=(\grave{e}_a, \grave{e}_e, \grave{e}_b, \grave{e}_h)$ for a given patient, a marginal space learning approach can be utilized, since a brute-force personalization of all $\dim(\theta)$ parameters at the same time might not be efficient and could lead to reduced accuracy in the estimated parameters. The marginal space learning pipeline of FIG. 13 focuses on the cardiac biomechanical model personalization for simpler presentation. Marginal space learning is done by decoupling the personalization of the biomechanical model parameters $\grave{e}_b$ from the electrophysiological ($\grave{e}_e$), anatomical ($\grave{e}_a$) and hemodynamical ($\grave{e}_h$) model personalization process. It is to be understood that the focus on one aspect (biomechanics) in the pipeline of FIG. 13 does not limit the approach, as it can be extended to the other components of the model as well.

Figure 14:
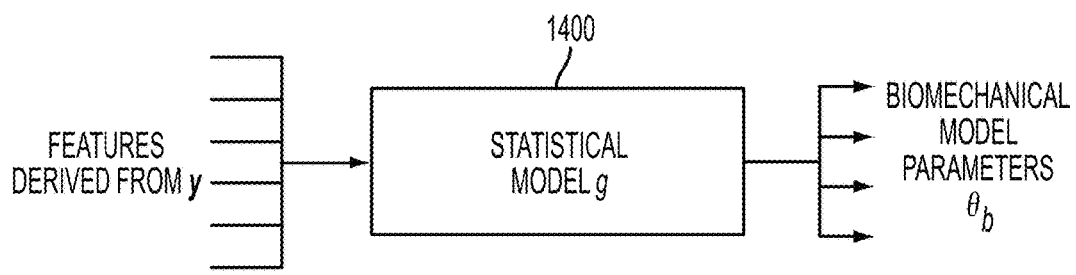
FIG. 14 illustrates an exemplary regression model for estimating cardiac biomechanical parameters.

Referring to FIG. 13, at 1310, the anatomical model parameters $\grave{e}_a$ are targeted by estimating a volumetric mesh representing the patient-specific anatomy including fiber architecture from a medical image data using a robust machine-learning approach, as described above in connection with step 204 of FIG. 2. At 1320, the electrophysiological model parameters $\grave{e}$ are adjusted to the clinical observations by using inverse problem methods utilizing clinical data such as ECG, endocardial mapping and dynamic images, or more efficiently by learning a backward ECG model using statistical learning techniques. At 1330, for the personalization of the biomechanical model parameters $\grave{e}_b$, a regression model that is trained based on all available simulations in the database DB is used to estimate biomechanical model parameters $\grave{e}_b$ based on features extracted from medical image data and clinical data of the patient. FIG. 14 illustrates an exemplary regression model for estimating cardiac biomechanical parameters. As shown in FIG. 14, the regression model 1400 is learning based statistical model g that is trained to estimate the biomechanical model parameters $\grave{e}_b$ based on input features derived from the dynamic electromechanical model y. The regression model for estimating the biomechanical model parameters $\grave{e}_b$ can be trained as described above in step 1204 of FIG. 12. Returning to FIG. 13, at 1340, the hemodynamic model (flow) $\grave{e}_h$ is personalized from clinical data directly by providing measured inflows and outflows as input to the hemodynamic model. The output of the model personalization is a patient-specific multi-physics heart model 1350.

According to another embodiment of the present invention, a two-step calibration-personalization approach can be used to personalize the parameters of the multi-physics computational heart model. The two-step calibration-personalization approach combines statistical learning techniques with generic optimization to refine the predicted parameters. In particular, in the first step a learned statistical model is utilized to provide an initial estimate of the electromechanical model parameters in order to calibrate the electromechanical model parameters. It can be assumed that the parameters estimated using the learned statistical model lie within the area of attraction of the global optimum of the particular personalization problem. Hence, in the second step, the machine-learning-based parameters serve as the initial starting point for an inverse optimization method, such as the inverse operation methods described above. Such an inverse optimization method can be based on, e.g., gradient-descent or more sophisticated gradient-free techniques utilizing a cost function that minimizes the discrepancy between measured and simulated heart motion. The output of the two-step approach is the personalized model, i.e. a set of optimal (with respect to a given cost function) patient-specific electromechanical model parameters.

When using features computed from simulated models for training, and features computed from a set of real clinical data for testing, a fundamental assumption in machine learning is being violated: Training and test data do not stem from the same distribution, since simulated data might not be fully comparable to real clinical data. Therefore, domain adaptation techniques can be used to adapt the trained model g to real clinical data. The Covariate Shift tackles this problem by re-weighting simulated samples during training based on the true domain distribution given by the real samples. Any classification or regression method that supports individual sample weights can be used in this approach. Other solutions to domain adaption utilize the concept of Transfer Learning in order to first learn a representation given simulated data and then learn the representation parameters for real data given the real samples. Thus, knowledge from the learning domain, where a sufficient number of samples is available, is transferred to the real domain, where we have only few samples. The latter approaches could potentially also be used to deal with missing data in the online estimation (e.g. in cases where no pressure measurements are available).

Besides transferring knowledge from one set of features to another (from simulated data to real data) as described above, another transfer is also covered: from forward model to forward model. There are several scenarios, where this transfer might be useful. Consider for instance the case, when we have a large database $DB_A$ compiled from simulations from a very detailed and thus computationally expensive forward model A, but intend to use a less complex model B for some reason (e.g. when one wants to sacrifice accuracy for reduced computation time during an initial phase in therapy planning). We can speed up the process of learning the inverse problem $g_B$ for the latter by re-using the large number of tuples from $DB_A$ and only creating a rather small database $DB_B$ for B, where $|DB_A|\gg|DB_B|$. We then need to transfer the set of features (domain) of $DB_A$ to the domain of $DB_B$, which can be achieved by utilizing transfer learning or domain adaptation techniques as described in the previous paragraph. Afterwards, we can include the transferred knowledge from $DB_A$ for learning $g_B$. Please note that the present invention is not limited to performing knowledge transfer from forward model to forward model by using the approach described above. Other techniques, which for instance use the inverse statistical model $g_A$ directly to improve $g_B$ could also provide significant benefits.

Returning to FIG. 12, at step 1208, uncertainty of the personalized parameters is estimated based on the training samples in the database. The intrinsic uncertainty of the described inverse problem, i.e. the uncertainty in the electromechanical model parameters, can be analyzed utilizing a database $DB=\{(y_i, \varphi_i, \grave{e}_i)|i=1 \ldots N\}$ of N simulations, where the inverse mapping g is known. Such a database including of a large number of simulations can be compiled as described above in step 1202. The features vectors $\{\varphi_i\}$ can be normalized component-wise among all entries in DB utilizing the z-score. The approach described herein allows for the computation of an upper bound on regression accuracy. First, an arbitrary tuple $(y', \varphi', è) \in DB$ is selected and the set $S_{\varphi'}$ of k nearest neighbors of $\varphi'$ among all $\varphi \in DB$ is computed. Now, for each $\varphi'' \in S_{\varphi'}$, the corresponding $è'' \in DB$ is looked up in the database and the variance $ó_{\varphi'}$ among those k parameter vectors is calculated. $ó_{\varphi'}$ is a good local estimate on the intrinsic uncertainty of the inverse electromechanical problem for large $N \to \infty$. To get a more global view on the intrinsic uncertainty of the problem, this procedure can be repeated for several points of interest in feature-space.

In addition to predicting the internal parameters è of the heart model the uncertainty in the prediction value can be estimated. The approach described above already provides an upper bound. According to an advantageous embodiment, a method which estimates the uncertainty associated with a prediction by a randomized tree regression model can be utilized. During training of a randomized tree regression model using a database of simulations, an ensemble of trees is grown. Within each tree, starting from its root node, the best split (based on a feature chosen from the set of all features $\varphi$ and a threshold) is chosen in order to maximize the information gain by splitting the training samples passed to the tree. This process is recursively repeated until the tree is grown to a user-specified depth. Each leaf will then contain a set of predictions, where for instance the mean of the predictions will be used as regression value later. As a measure of uncertainty, the variation of the predictions within one leaf (or as a linear combination of multiple leafs from different trees) can be calculated.

Figure 15:
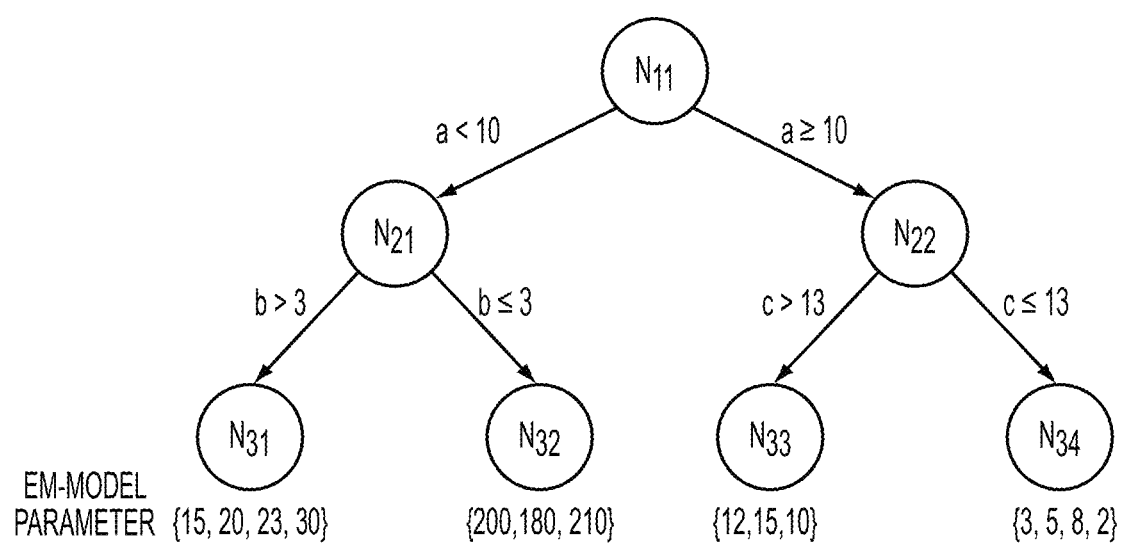
FIG. 15 illustrates an example of a regression tree to estimate an electromechanical (EM) model parameter based on the computed features.

FIG. 15 illustrates a simple example of a regression tree for demonstration purposes, which is suited to estimate an imaginary one-dimensional electromechanical (EM) model parameter based on the computed features $\varphi$. During test time, an unseen sample $\varphi^*$ is passed through the tree and reaches a leaf node where a set of predicted values created during training for the imaginary parameter is available. If this sample contains $(a=5; b=10) \in \varphi^*$ as feature values, it will reach leaf node $N_{31}$. The prediction for the imaginary parameter would then be the mean of the predictions in $N_{31}$: $(15+20+23+30)/4=22$, and the uncertainty can be computed as the standard deviation: $\sqrt{(15-22)^2+(20-22)^2+(23-22)^2+(30-22)^2}=5.43$. In the real scenario, an ensemble of trees has to be traversed for each sample and the resulting uncertainty measures must be aggregated (e.g., averaged).

Returning to FIG. 12, at step 1210 the database of training samples is updated. In particular, once the parameters of the multi-physics heart model are personalized the resulting patient-specific multi-physics heart model can be stored in the database and used as an additional training sample to re-train the learning-based statistical model. At step 1212, the estimated model parameters and their uncertainty are visualized. For example, the estimated parameters and their uncertainty can be visualized through 3D, color-coded maps, tables, and spatial/temporal plots.

Figure 16:
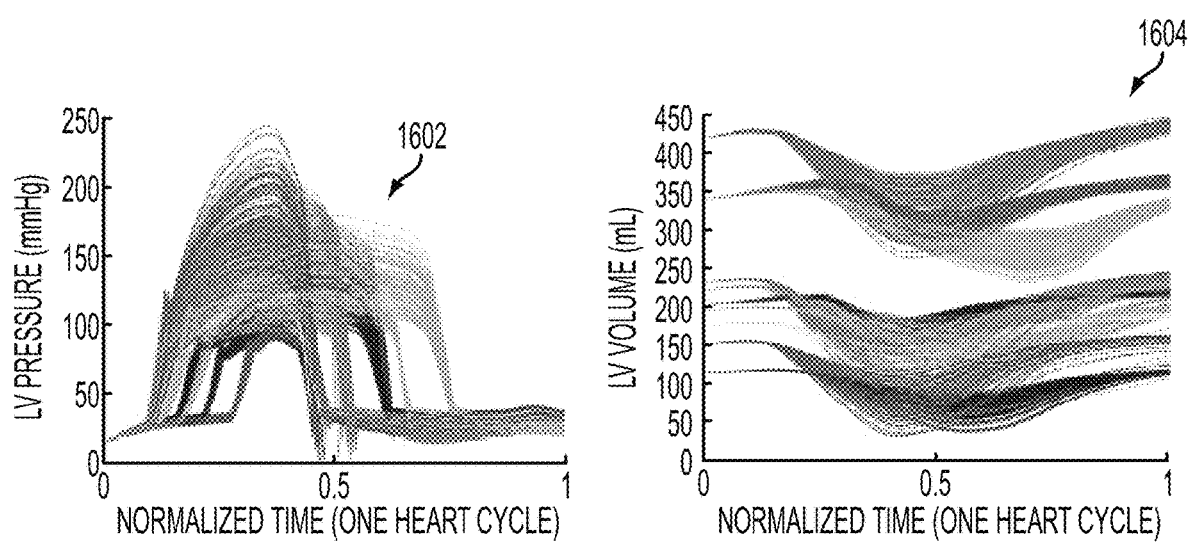
FIG. 16 illustrates variations in simulated pressure curves and volume curves of the left ventricle over an entire database.
Figure 17:
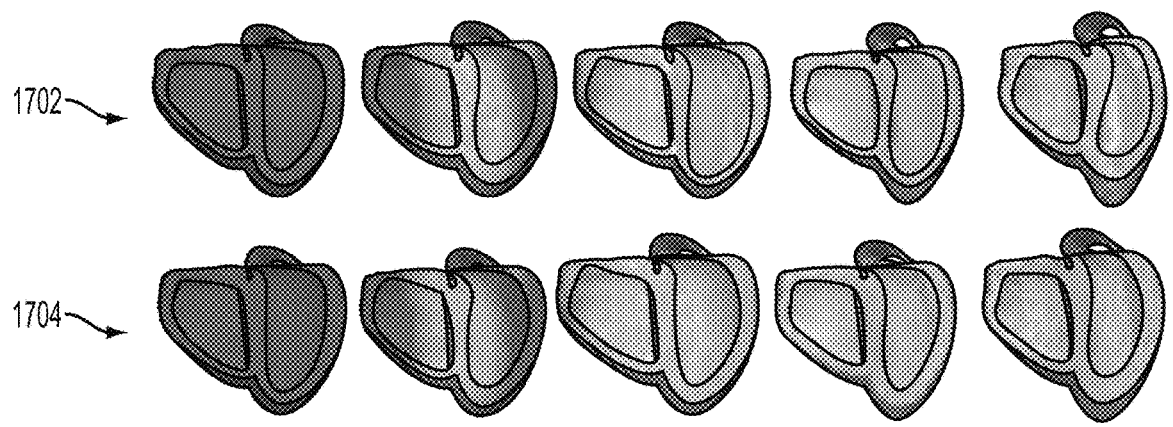
FIG. 17 illustrates exemplary 3D representations of deformed anatomy at different points in time from the temporal sequences of simulations.

Exemplary results on regression accuracy were computed by the present inventors using leave-one-patient-out cross validation on a training database DB of N=1500 simulations stemming from 10 patients suffering from dilated cardiomyopathy (DCM). The present inventors focused on the estimation of two biomechanical parameters in this experiment, namely one parameter of the active stress: the maximum contraction of myocytes in the left ventricle $ó_{LV}$, and one passive property: the Young's modulus E. For each patient, 150 simulations were computed using the data generation workflow described in step 1202 of FIG. 12. For both parameters of interest ($ó_{LV}$ and E), their values were varied by ±30% of the calibrated value. Over all patients, $ó_{LV}$ ranged from 105 kPa to 363 kPa, and E ranged from 210 kPa to 541 kPa. The values for $ó_{LV}$ and E were drawn from uniform distributions defined by the ranges mentioned above. To capture variability in atrial and arterial pressure observed in patients, the present inventors also varied the pre-load and post-load parameters of the model by ±10%. FIG. 16 illustrates variations in pressure curves 1602 and volume curves 1604 of the left ventricle over the entire database. FIG. 17 illustrates exemplary 3D representations of the deformed anatomy at different points in time from the temporal sequences of simulations performed using a large value for $ó_{LV}$ (row 1702) and a small value for $ó_{LV}$ (row 1704), while E and all the other parameters in è remain constant. In FIG. 17, the simulations in row 1702 are performed with $ó_{LV}$=360 kPa and the simulations in row 1704 are performed with $ó_{LV}$=190 kPa.

Three different statistical learning techniques (Random Forest, Gradient Boosting and First Order Polynomial Regression) were tested. The results are shown in. Table 1 and Table 2 as absolute errors of the predicted value versus the ground truth value. For the active parameter $\sigma_{LV}$, polynomial regression achieves the best results with a mean error of less than 8% of the full range of $\sigma_{LV}$ parameters used for creating the database DB, while Random Forest regression yields the best results for the passive parameter E with a mean error of approximately 14% with respect to the range of all E values in DB. These results demonstrate the feasibility of the proposed data-driven approach for parameter estimation.

TABLE 1

Preliminary results for the regression accuracy of the active parameter $\sigma_{LV}$ [kPa]

| | $\sigma_{LV}$ | | | | | |
| --- | --- | --- | --- | --- | --- | --- |
| | Testing | | | Training | | |
| Method | Mean | Std | Max | Mean | Std | Max |
| Random Forest | 32.6 | 22.1 | 94.5 | 3.58 | 3.24 | 24.6 |
| Gradient Boosting | 31.4 | 24.9 | 119 | 2.52 | 1.96 | 12.2 |
| Polynomial Regression | 19.3 | 16.9 | 128 | 9.94 | 9.03 | 66.4 |

TABLE 2

Preliminary results for the regression accuracy of the passive property E [kPa]

| | E | | | | | |
| --- | --- | --- | --- | --- | --- | --- |
| | Testing | | | Training | | |
| Method | Mean | Std | Max | Mean | Std | Max |
| Random Forest | 47.4 | 35 | 179 | 7.58 | 6.42 | 63.1 |
| Gradient Boosting | 66 | 43.9 | 218 | 5.29 | 4.19 | 25.7 |
| Polynomial Regression | 134 | 85.9 | 485 | 24 | 21.2 | 179 |

Given the above described framework for machine-learning based parameter estimation, embodiments of the present invention are not limited to only estimating patient-specific global, regional, or spatial parameters, but can also perform coarse-to-fine personalization strategies such as patch-wise manifold learning (learn a statistical model for each region) with spatial constraints using localized features (regional motion, regional strain, etc.). Although embodiments of the present invention are utilized for estimating parameters for cardiac electromechanics, the present invention is not limited thereto and may be similarly applied to any organ and function, such as mitral or aortic valve, liver, lung, etc. The above described approach can also be used for elasticity and viscosity estimation from shear-wave imaging. In this case, the model would be the sheer-wave propagation model, and the features being observed would be displacement maps.

Figure 18:
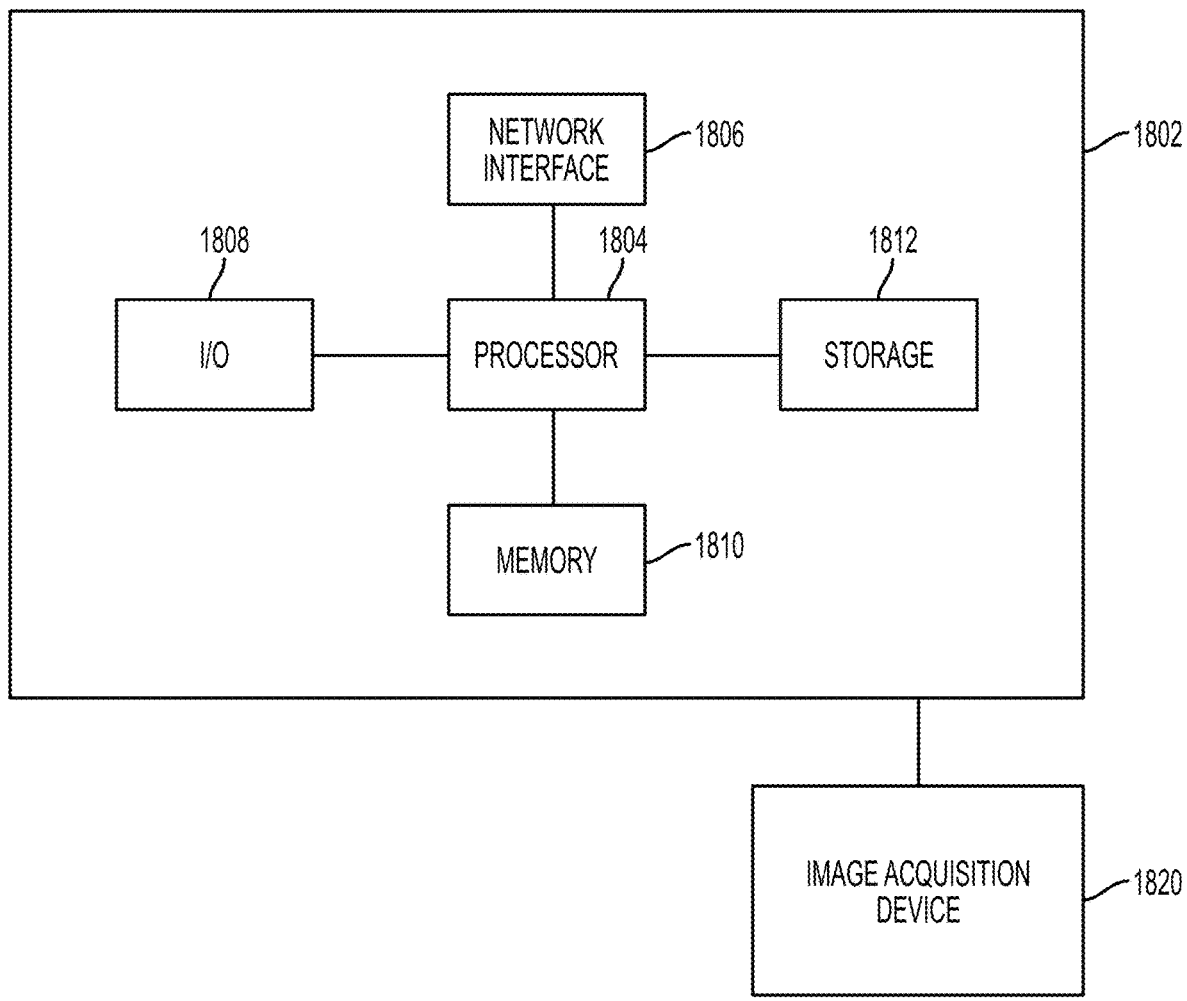
FIG. 18 is a high-level block diagram of a computer capable of implementing the present invention.

The above-described methods for simulating cardiac function and personalizing parameters of a multi-physics computations heart model can be implemented on a computer using well-known computer processors, memory units, storage devices, computer software, and other components. A high-level block diagram of such a computer is illustrated in FIG. 18. Computer 1802 contains a processor 1804, which controls the overall operation of the computer 1802 by executing computer program instructions which define such operation. The computer program instructions may be stored in a storage device 1812 (e.g., magnetic disk) and loaded into memory 1810 when execution of the computer program instructions is desired. Thus, the steps of the methods of FIGS. 1, 2, 3, 5, 7, 8, 12, and 13 may be defined by the computer program instructions stored in the memory 1810 and/or storage 1812 and controlled by the processor 1804 executing the computer program instructions. An image acquisition device 1820, such as a CT scanning device, C-arm image acquisition device, MR scanning device, Ultrasound device, etc., can be connected to the computer 1802 to input image data to the computer 1802. It is possible to implement the image acquisition device 1820 and the computer 1802 as one device. It is also possible that the image acquisition device 1820 and the computer 1802 communicate wirelessly through a network. The computer 1802 also includes one or more network interfaces 1806 for communicating with other devices via a network. The computer 1802 also includes other input/output devices 1808 that enable user interaction with the computer 1802 (e.g., display, keyboard, mouse, speakers, buttons, etc.). Such input/output devices 1808 may be used in conjunction with a set of computer programs as an annotation tool to annotate volumes received from the image acquisition device 1820. One skilled in the art will recognize that an implementation of an actual computer could contain other components as well, and that FIG. 18 is a high level representation of some of the components of such a computer for illustrative purposes.

The foregoing Detailed Description is to be understood as being in every respect illustrative and exemplary, but not restrictive, and the scope of the invention disclosed herein is not to be determined from the Detailed Description, but rather from the claims as interpreted according to the full breadth permitted by the patent laws. It is to be understood that the embodiments shown and described herein are only illustrative of the principles of the present invention and that various modifications may be implemented by those skilled in the art without departing from the scope and spirit of the invention. Those skilled in the art could implement various other feature combinations without departing from the scope and spirit of the invention.

The invention claimed is:

1. A method for computing cardiac function of a patient, comprising:
   generating a patient-specific anatomical model of a heart from medical image data of the patient;
   generating a patient-specific multi-physics computational heart model based on the patient-specific anatomical model by personalizing parameters of a cardiac electrophysiology model, a cardiac biomechanics model, and a cardiac hemodynamics model using a marginal approach based on the medical image data and clinical measurements of the patient, wherein the parameters for the cardiac hemodynamics model are personalized by:
      synchronizing at least one cardiac cycle of an arterial pressure measurement of the patient with at least one cardiac cycle of an arterial inflow estimated from the medical image data, and
      comparing the synchronized arterial pressure measurement with calculated arterial pressure values;
   computing cardiac function of the patient using the patient-specific multi-physics computational heart model to estimate patient parameters; and
   outputting the estimated patient parameters.

2. The method of claim 1, wherein generating a patient-specific multi-physics computational heart model based on the patient-specific anatomical model by personalizing parameters of a cardiac electrophysiology model, a cardiac biomechanics model, and a cardiac hemodynamics model using a marginal approach based on the medical image data and clinical measurements of the patient comprises:
   personalizing the parameters of at least one of the cardiac electrophysiology model, the cardiac biomechanics model, and the cardiac hemodynamics model based on the medical image data and the clinical measurements of the patient using inverse problem algorithms based on forward simulations of the cardiac electrophysiology model, the cardiac biomechanics model, and the cardiac hemodynamics model.

3. The method of claim 2, wherein personalizing the parameters of at least one of the cardiac electrophysiology model, the cardiac biomechanics model, and the cardiac hemodynamics model based on the medical image data and the clinical measurements of the patient using inverse problem algorithms based on forward simulations of the cardiac electrophysiology model, the cardiac biomechanics model, and the cardiac hemodynamics model comprises:
   personalizing the parameters of the cardiac hemodynamics model by estimating parameters of Windkessel models representing arteries for the cardiac hemodynamic model based on the arterial pressure measurement of the patient and blood pool volume or blood flow measurements in the medical image data of the patient.

4. The method of claim 3, wherein:
   the medical image data comprises 4D medical image data,
   synchronizing at least one cardiac cycle of an arterial pressure measurement of the patient with at least one cardiac cycle of an arterial inflow estimated from the medical image data comprises:
      selecting a cardiac cycle from the arterial pressure measurement, resulting in a pressure curve for the selected cardiac cycle,
      stretching a systolic portion of the pressure curve such that an ejection time in the pressure curve is equal to an ejection time in a volume curve resulting from estimating the blood pool volume in each of a plurality of frames in the 4D medical image data, and
      shifting the pressure curve to synchronize the pressure curve with the volume curve; and
   comparing the synchronized arterial pressure measurement with calculated arterial pressure values comprises:
      minimizing a cost function that compares the synchronized arterial pressure measurement and the calculated arterial pressure calculated using a Windkessel model based on an arterial inflow estimate from the medical image data to estimate the parameters of the Windkessel models.

5. The method of claim 2, wherein personalizing the parameters of at least one of the cardiac electrophysiology model, the cardiac biomechanics model, and the cardiac hemodynamics model based on the medical image data and the clinical measurements of the patient using inverse problem algorithms based on forward simulations of the cardiac electrophysiology model, the cardiac biomechanics model, and the cardiac hemodynamics model comprises:

personalizing parameters of the cardiac electrophysiology model by estimating parameters including tissue diffusivity parameters and action potential duration based on at least one of a clinical ECG signal, an endocardial mapping, or a body surface mapping of the patient.

6. The method of claim 5, wherein personalizing parameters of the cardiac electrophysiology model by estimating parameters including tissue diffusivity parameters and action potential duration based on at least one of a clinical ECG signal, an endocardial mapping, or a body surface mapping of the patient comprises:

calculating personalized tissue diffusivity parameters for left ventricle, right ventricle, and myocardium regions by minimizing cost functions that compare ECG features resulting from cardiac electrophysiology simulations with measured ECG features; and calculating the action potential duration based on a difference between measured ECG features and computed ECG features resulting from cardiac electrophysiology simulations.

7. The method of claim 2, wherein personalizing the parameters of at least one of the cardiac electrophysiology model, the cardiac biomechanics model, and the cardiac hemodynamics model based on the medical image data and the clinical measurements of the patient using inverse problem algorithms based on forward simulations of the cardiac electrophysiology model, the cardiac biomechanics model, and the cardiac hemodynamics model comprises:

personalizing the parameters of the cardiac biomechanics model by estimating personalized parameters including a maximum active contraction, tissue stiffness, and a pulmonary vein pressure for the cardiac biomechanics model based on pressure and volume features derived from the medical image data and the clinical measurements of the patient.

8. The method of claim 7, wherein personalizing the parameters of the cardiac biomechanics model by estimating personalized parameters including a maximum active contraction, tissue stiffness, and a pulmonary vein pressure for the cardiac biomechanics model based on pressure and volume features derived from the medical image data and the clinical measurements of the patient comprises:

calculating the personalized pulmonary vein pressure based on a difference between a minimum measured pressure value and a minimum calculated pressure value resulting from an electromechanical simulation; and calculating the personalized maximum active contraction and tissue stiffness by minimizing a cost function that measures a similarity of measured pressure and volume curves and calculated pressure and volume curves resulting from an electromechanical simulation by comparing a weighted sum of features derived from the measured and calculated pressure and volume curves.

9. The method of claim 1, wherein generating a patient-specific multi-physics computational heart model based on the patient-specific anatomical model by personalizing parameters of a cardiac electrophysiology model, a cardiac biomechanics model, and a cardiac hemodynamics model using a marginal approach based on the medical image data and clinical measurements of the patient comprises:

estimating the personalized parameters for the cardiac electrophysiology model, the cardiac biomechanics model, and the cardiac hemodynamics model using a trained regression model trained on a database of training samples based on features extracted from the medical image data and the clinical measurements of the patient.

10. The method of claim 1, wherein generating a patient-specific multi-physics computational heart model based on the patient-specific anatomical model by personalizing parameters of a cardiac electrophysiology model, a cardiac biomechanics model, and a cardiac hemodynamics model using a marginal approach based on the medical image data and clinical measurements of the patient comprises:

for each of the cardiac electrophysiology model, the cardiac biomechanics model, and the cardiac hemodynamics model, estimating the personalized parameters using a respective trained regression model.

11. The method of claim 1, wherein generating a patient-specific multi-physics computational heart model based on the patient-specific anatomical model by personalizing parameters of a cardiac electrophysiology model, a cardiac biomechanics model, and a cardiac hemodynamics model using a marginal approach based on the medical image data and clinical measurements of the patient comprises:

estimating the personalized parameters for a first one of the cardiac electrophysiology model, the cardiac biomechanics model, and the cardiac hemodynamics model using a trained regression model; and estimating the personalized parameters of a second one of the cardiac electrophysiology model, the cardiac biomechanics model, and the cardiac hemodynamics model using an inverse problem algorithm based on forward model simulations.

12. The method of claim 1, wherein the features include one or more of ejection fraction; stroke volume; minimum, maximum, mean, and standard deviation left ventricle pressure; minimum, maximum, mean, and standard deviation left ventricle volume; minimum, maximum, mean, and standard deviation left atrium pressure; minimum, maximum, mean, and standard deviation left atrium volume; minimum, maximum, mean, and standard deviation artery pressure; minimum, maximum, mean, and standard deviation blood flow; shape descriptors; cardiac dynamics descriptors; and electrophysiology descriptors.

13. The method of claim 1, wherein generating a patient-specific multi-physics computational heart model based on the patient-specific anatomical model by personalizing parameters of a cardiac electrophysiology model, a cardiac biomechanics model, and a cardiac hemodynamics model using a marginal approach based on the medical image data and clinical measurements of the patient further comprises:

calculating uncertainties for the personalized parameters by finding for each of the personalized parameters, a respective k-closest dataset in the database of training samples and estimating a mean and standard deviation for each of the personalized parameters using the respective k-closest dataset.

14. The method of claim 1, wherein generating a patient-specific multi-physics computational heart model based on the patient-specific anatomical model by personalizing parameters of a cardiac electrophysiology model, a cardiac biomechanics model, and a cardiac hemodynamics model using a marginal approach based on the medical image data and clinical measurements of the patient comprises:
calibrating the parameters of the cardiac electrophysiology model, cardiac biomechanics model, and cardiac hemodynamics model by calculating initial estimates for the parameters using a trained regression model; and
estimating personalized parameters of the cardiac electrophysiology model, the cardiac biomechanics model, and the cardiac hemodynamics model using inverse problem algorithms based on forward simulations of the cardiac electrophysiology model, the cardiac biomechanics model, and the cardiac hemodynamics model with the initial estimates of the parameters used as starting points for the forward simulations.

15. The method of claim 9, wherein the training samples in the database of training samples are generated using a forward model of cardiac electrophysiology by varying model parameters to generate a plurality of training samples for each of a plurality of patient data.

16. An apparatus for computing cardiac function of a patient, comprising:
a processor; and
a memory to store computer program instructions, the computer program instructions when executed on the processor cause the processor to perform operations comprising:
generating a patient-specific anatomical model of a heart from medical image data of the patient;
generating a patient-specific multi-physics computational heart model based on the patient-specific anatomical model by personalizing parameters of a cardiac electrophysiology model, a cardiac biomechanics model, and a cardiac hemodynamics model using a marginal approach based on the medical image data and clinical measurements of the patient, wherein the parameters for the cardiac hemodynamics model are personalized by:
synchronizing at least one cardiac cycle of an arterial pressure measurement of the patient with at least one cardiac cycle of an arterial inflow estimated from the medical image data, and
comparing the synchronized arterial pressure measurement with calculated arterial pressure values;
computing cardiac function of the patient using the patient-specific multi-physics computational heart model to estimate patient parameters; and
outputting the estimated patient parameters.

17. The apparatus of claim 16, wherein generating a patient-specific multi-physics computational heart model based on the patient-specific anatomical model by personalizing parameters of a cardiac electrophysiology model, a cardiac biomechanics model, and a cardiac hemodynamics model using a marginal approach based on the medical image data and clinical measurements of the patient comprises:
personalizing the parameters of at least one of the cardiac electrophysiology model, the cardiac biomechanics model, and the cardiac hemodynamics model based on the medical image data and the clinical measurements of the patient using inverse problem algorithms based on forward simulations of the cardiac electrophysiology model, the cardiac biomechanics model, and the cardiac hemodynamics model.

18. The apparatus of claim 17, wherein personalizing the parameters of at least one of the cardiac electrophysiology model, the cardiac biomechanics model, and the cardiac hemodynamics model based on the medical image data and the clinical measurements of the patient using inverse problem algorithms based on forward simulations of the cardiac electrophysiology model, the cardiac biomechanics model, and the cardiac hemodynamics model comprises:
personalizing the parameters of the cardiac hemodynamics model by estimating parameters of Windkessel models representing arteries for the cardiac hemodynamic model based on the arterial pressure measurement of the patient and blood pool volume or blood flow measurements in the medical image data of the patient.

19. The apparatus of claim 18, wherein:
the medical image data comprises 4D medical image data,
synchronizing at least one cardiac cycle of an arterial pressure measurement of the patient with at least one cardiac cycle of an arterial inflow estimated from the medical image data comprises:
selecting a cardiac cycle from the arterial pressure measurement, resulting in a pressure curve for the selected cardiac cycle,
stretching a systolic portion of the pressure curve such that an ejection time in the pressure curve is equal to an ejection time in a volume curve resulting from estimating the blood pool volume in each of a plurality of frames in the 4D medical image data, and
shifting the pressure curve to synchronize the pressure curve with the volume curve; and
comparing the synchronized arterial pressure measurement with calculated arterial pressure values comprises:
minimizing a cost function that compares the synchronized arterial pressure measurement and the calculated arterial pressure calculated using a Windkessel model based on an arterial inflow estimate from the medical image data to estimate the parameters of the Windkessel models.

20. The apparatus of claim 17, wherein personalizing the parameters of at least one of the cardiac electrophysiology model, the cardiac biomechanics model, and the cardiac hemodynamics model based on the medical image data and the clinical measurements of the patient using inverse problem algorithms based on forward simulations of the cardiac electrophysiology model, the cardiac biomechanics model, and the cardiac hemodynamics model comprises:
personalizing parameters of the cardiac electrophysiology model by estimating parameters including tissue diffusivity parameters and action potential duration based on at least one of a clinical ECG signal, an endocardial mapping, or a body surface mapping of the patient.

21. The apparatus of claim 20, wherein personalizing parameters of the cardiac electrophysiology model by estimating parameters including tissue diffusivity parameters and action potential duration based on at least one of a clinical ECG signal, an endocardial mapping, or a body surface mapping of the patient comprises:
calculating personalized tissue diffusivity parameters for left ventricle, right ventricle, and myocardium regions by minimizing cost functions that compare ECG features resulting from cardiac electrophysiology simulations with measured ECG features; and calculating the action potential duration based on a difference between measured ECG features and computed ECG features resulting from cardiac electrophysiology simulations.

22. The apparatus of claim 17, wherein personalizing the parameters of at least one of the cardiac electrophysiology model, the cardiac biomechanics model, and the cardiac hemodynamics model based on the medical image data and the clinical measurements of the patient using inverse problem algorithms based on forward simulations of the cardiac electrophysiology model, the cardiac biomechanics model, and the cardiac hemodynamics model comprises:
personalizing the parameters of the cardiac biomechanics model by estimating personalized parameters including a maximum active contraction, tissue stiffness, and a pulmonary vein pressure for the cardiac biomechanics model based on pressure and volume features derived from the medical image data and the clinical measurements of the patient.

23. The apparatus of claim 22, wherein personalizing the parameters of the cardiac biomechanics model by estimating personalized parameters including a maximum active contraction, tissue stiffness, and a pulmonary vein pressure for the cardiac biomechanics model based on pressure and volume features derived from the medical image data and the clinical measurements of the patient comprises:
calculating the personalized pulmonary vein pressure based on a difference between a minimum measured pressure value and a minimum calculated pressure value resulting from an electromechanical simulation; and
calculating the personalized maximum active contraction and tissue stiffness by minimizing a cost function that measures a similarity of measured pressure and volume curves and calculated pressure and volume curves resulting from an electromechanical simulation by comparing a weighted sum of features derived from the measured and calculated pressure and volume curves.

24. The apparatus of claim 16, wherein generating a patient-specific multi-physics computational heart model based on the patient-specific anatomical model by personalizing parameters of a cardiac electrophysiology model, a cardiac biomechanics model, and a cardiac hemodynamics model using a marginal approach based on the medical image data and clinical measurements of the patient comprises:
estimating the personalized parameters for the cardiac electrophysiology model, the cardiac biomechanics model, and the cardiac hemodynamics model using a trained regression model trained on a database of training samples based on features extracted from the medical image data and the clinical measurements of the patient.

25. The apparatus of claim 16, wherein generating a patient-specific multi-physics computational heart model based on the patient-specific anatomical model by personalizing parameters of a cardiac electrophysiology model, a cardiac biomechanics model, and a cardiac hemodynamics model using a marginal approach based on the medical image data and clinical measurements of the patient comprises:
estimating the personalized parameters using a respective trained regression model for each of the cardiac electrophysiology model, the cardiac biomechanics model, and the cardiac hemodynamics model.

26. The apparatus of claim 16, wherein generating a patient-specific multi-physics computational heart model based on the patient-specific anatomical model by personalizing parameters of a cardiac electrophysiology model, a cardiac biomechanics model, and a cardiac hemodynamics model using a marginal approach based on the medical image data and clinical measurements of the patient comprises:
estimating the personalized parameters for a first one of the cardiac electrophysiology model, the cardiac biomechanics model, and the cardiac hemodynamics model using a trained regression model; and
estimating the personalized parameters of a second one of the cardiac electrophysiology model, the cardiac biomechanics model, and the cardiac hemodynamics model using an inverse problem algorithm based on forward model simulations.

27. The apparatus of claim 16, wherein the features include one or more of ejection fraction; stroke volume; minimum, maximum, mean, and standard deviation left ventricle pressure; minimum, maximum, mean, and standard deviation left ventricle volume; minimum, maximum, mean, and standard deviation left atrium pressure; minimum, maximum, mean, and standard deviation left atrium volume; minimum, maximum, mean, and standard deviation artery pressure; minimum, maximum, mean, and standard deviation blood flow; shape descriptors; cardiac dynamics descriptors; and electrophysiology descriptors.

28. The apparatus of claim 16, wherein generating a patient-specific multi-physics computational heart model based on the patient-specific anatomical model by personalizing parameters of a cardiac electrophysiology model, a cardiac biomechanics model, and a cardiac hemodynamics model using a marginal approach based on the medical image data and clinical measurements of the patient further comprises:
calculating uncertainties for the personalized parameters by finding for each of the personalized parameters, a respective k-closest dataset in the database of training samples and estimating a mean and standard deviation for each of the personalized parameters using the respective k-closest dataset.

29. The apparatus of claim 16, wherein generating a patient-specific multi-physics computational heart model based on the patient-specific anatomical model by personalizing parameters of a cardiac electrophysiology model, a cardiac biomechanics model, and a cardiac hemodynamics model using a marginal approach based on the medical image data and clinical measurements of the patient comprises:
calibrating the parameters of the cardiac electrophysiology model, cardiac biomechanics model, and cardiac hemodynamics model by calculating initial estimates for the parameters using a trained regression model; and
estimating personalized parameters of the cardiac electrophysiology model, the cardiac biomechanics model, and the cardiac hemodynamics model using inverse problem algorithms based on forward simulations of the cardiac electrophysiology model, the cardiac biomechanics model, and the cardiac hemodynamics model with the initial estimates of the parameters used as starting points for the forward simulations.

30. The apparatus of claim 24, wherein the training samples in the database of training samples are generated using a forward model of cardiac electrophysiology by varying model parameters to generate a plurality of training samples for each of a plurality of patient data.

31. A non-transitory computer readable medium storing computer program instructions for computing cardiac function of a patient, the computer program instructions when executed by a processor, cause the processor to performed operations comprising:
- generating a patient-specific anatomical model of a heart from medical image data of the patient;
- generating a patient-specific multi-physics computational heart model based on the patient-specific anatomical model by personalizing parameters of a cardiac electrophysiology model, a cardiac biomechanics model, and a cardiac hemodynamics model using a marginal approach based on the medical image data and clinical measurements of the patient, wherein the parameters for the cardiac hemodynamics model are personalized by:
  - synchronizing at least one cardiac cycle of an arterial pressure measurement of the patient with at least one cardiac cycle of an arterial inflow estimated from the medical image data, and
  - comparing the synchronized arterial pressure measurement with calculated arterial pressure values;
- computing cardiac function of the patient using the patient-specific multi-physics computational heart model to estimate patient parameters; and
- outputting the estimated patient parameters.

32. The non-transitory computer readable medium of claim 31, wherein generating a patient-specific multi-physics computational heart model based on the patient-specific anatomical model by personalizing parameters of a cardiac electrophysiology model, a cardiac biomechanics model, and a cardiac hemodynamics model using a marginal approach based on the medical image data and clinical measurements of the patient comprises:
- personalizing the parameters of at least one of the cardiac electrophysiology model, the cardiac biomechanics model, and the cardiac hemodynamics model based on the medical image data and the clinical measurements of the patient using inverse problem algorithms based on forward simulations of the cardiac electrophysiology model, the cardiac biomechanics model, and the cardiac hemodynamics model.

33. The non-transitory computer readable medium of claim 32, wherein personalizing the parameters of at least one of the cardiac electrophysiology model, the cardiac biomechanics model, and the cardiac hemodynamics model based on the medical image data and the clinical measurements of the patient using inverse problem algorithms based on forward simulations of the cardiac electrophysiology model, the cardiac biomechanics model, and the cardiac hemodynamics model comprises:
- personalizing the parameters of the cardiac hemodynamics model by estimating parameters of Windkessel models representing arteries for the cardiac hemodynamic model based on the arterial pressure measurement of the patient and blood pool volume or blood flow measurements in the medical image data of the patient.

34. The non-transitory computer readable medium of claim 33, wherein:
- the medical image data comprises 4D medical image data,
- synchronizing at least one cardiac cycle of an arterial pressure measurement of the patient with at least one cardiac cycle of an arterial inflow estimated from the medical image data comprises:
  - selecting a cardiac cycle from the arterial pressure measurement, resulting in a pressure curve for the selected cardiac cycle,
  - stretching a systolic portion of the pressure curve such that an ejection time in the pressure curve is equal to an ejection time in a volume curve resulting from estimating the blood pool volume in each of a plurality of frames in the 4D medical image data, and
  - shifting the pressure curve to synchronize the pressure curve with the volume curve; and
- comparing the synchronized arterial pressure measurement with calculated arterial pressure values comprises:
  - minimizing a cost function that compares the synchronized arterial pressure measurement and the calculated arterial pressure calculated using a Windkessel model based on an arterial inflow estimate from the medical image data to estimate the parameters of the Windkessel models.

35. The non-transitory computer readable medium of claim 32, wherein personalizing the parameters of at least one of the cardiac electrophysiology model, the cardiac biomechanics model, and the cardiac hemodynamics model based on the medical image data and the clinical measurements of the patient using inverse problem algorithms based on forward simulations of the cardiac electrophysiology model, the cardiac biomechanics model, and the cardiac hemodynamics model comprises:
- personalizing parameters of the cardiac electrophysiology model by estimating parameters including tissue diffusivity parameters and action potential duration based on at least one of a clinical ECG signal, an endocardial mapping, or a body surface mapping of the patient.

36. The non-transitory computer readable medium of claim 35, wherein personalizing parameters of the cardiac electrophysiology model by estimating parameters including tissue diffusivity parameters and action potential duration based on at least one of a clinical ECG signal, an endocardial mapping, or a body surface mapping of the patient comprises:
- calculating personalized tissue diffusivity parameters for left ventricle, right ventricle, and myocardium regions by minimizing cost functions that compare ECG features resulting from cardiac electrophysiology simulations with measured ECG features; and
- calculating the action potential duration based on a difference between measured ECG features and computed ECG features resulting from cardiac electrophysiology simulations.

37. The non-transitory computer readable medium of claim 32, wherein personalizing the parameters of at least one of the cardiac electrophysiology model, the cardiac biomechanics model, and the cardiac hemodynamics model based on the medical image data and the clinical measurements of the patient using inverse problem algorithms based on forward simulations of the cardiac electrophysiology model, the cardiac biomechanics model, and the cardiac hemodynamics model comprises:
- personalizing the parameters of the cardiac biomechanics model by estimating personalized parameters including a maximum active contraction, tissue stiffness, and a pulmonary vein pressure for the cardiac biomechanics model based on pressure and volume features derived from the medical image data and the clinical measurements of the patient.

38. The non-transitory computer readable medium of claim 37, wherein personalizing the parameters of the cardiac biomechanics model by estimating personalized parameters including a maximum active contraction, tissue stiffness, and a pulmonary vein pressure for the cardiac biomechanics model based on pressure and volume features derived from the medical image data and the clinical measurements of the patient comprises:

calculating the personalized pulmonary vein pressure based on a difference between a minimum measured pressure value and a minimum calculated pressure value resulting from an electromechanical simulation; and calculating the personalized maximum active contraction and tissue stiffness by minimizing a cost function that measures a similarity of measured pressure and volume curves and calculated pressure and volume curves resulting from an electromechanical simulation by comparing a weighted sum of features derived from the measured and calculated pressure and volume curves.

39. The non-transitory computer readable medium of claim 31, wherein generating a patient-specific multi-physics computational heart model based on the patient-specific anatomical model by personalizing parameters of a cardiac electrophysiology model, a cardiac biomechanics model, and a cardiac hemodynamics model using a marginal approach based on the medical image data and clinical measurements of the patient comprises:

estimating the personalized parameters for the cardiac electrophysiology model, the cardiac biomechanics model, and the cardiac hemodynamics model using a trained regression model trained on a database of training samples based on features extracted from the medical image data and the clinical measurements of the patient.

40. The non-transitory computer readable medium of claim 31, wherein generating a patient-specific multi-physics computational heart model based on the patient-specific anatomical model by personalizing parameters of a cardiac electrophysiology model, a cardiac biomechanics model, and a cardiac hemodynamics model using a marginal approach based on the medical image data and clinical measurements of the patient comprises:

for each of the cardiac electrophysiology model, the cardiac biomechanics model, and the cardiac hemodynamics model, estimating the personalized parameters using a respective trained regression model.

41. The non-transitory computer readable medium of claim 31, wherein generating a patient-specific multi-physics computational heart model based on the patient-specific anatomical model by personalizing parameters of a cardiac electrophysiology model, a cardiac biomechanics model, and a cardiac hemodynamics model using a marginal approach based on the medical image data and clinical measurements of the patient comprises:

estimating the personalized parameters for a first one of the cardiac electrophysiology model, the cardiac biomechanics model, and the cardiac hemodynamics model using a trained regression model; and estimating the personalized parameters of a second one of the cardiac electrophysiology model, the cardiac biomechanics model, and the cardiac hemodynamics model, and the cardiac hemodynamics model using an inverse problem algorithm based on forward model simulations.

42. The non-transitory computer readable medium of claim 31, wherein the features include one or more of ejection fraction; stroke volume; minimum, maximum, mean, and standard deviation left ventricle pressure; minimum, maximum, mean, and standard deviation left ventricle volume; minimum, maximum, mean, and standard deviation left atrium pressure; minimum, maximum, mean, and standard deviation left atrium volume; minimum, maximum, mean, and standard deviation artery pressure; minimum, maximum, mean, and standard deviation blood flow; shape descriptors; cardiac dynamics descriptors; and electrophysiology descriptors.

43. The non-transitory computer readable medium of claim 31, wherein generating a patient-specific multi-physics computational heart model based on the patient-specific anatomical model by personalizing parameters of a cardiac electrophysiology model, a cardiac biomechanics model, and a cardiac hemodynamics model using a marginal approach based on the medical image data and clinical measurements of the patient further comprises:

calculating uncertainties for the personalized parameters by finding for each of the personalized parameters, a respective k-closest dataset in the database of training samples and estimating a mean and standard deviation for each of the personalized parameters using the respective k-closest dataset.

44. The non-transitory computer readable medium of claim 31, wherein generating a patient-specific multi-physics computational heart model based on the patient-specific anatomical model by personalizing parameters of a cardiac electrophysiology model, a cardiac biomechanics model, and a cardiac hemodynamics model using a marginal approach based on the medical image data and clinical measurements of the patient comprises:

calibrating the parameters of the cardiac electrophysiology model, cardiac biomechanics model, and cardiac hemodynamics model by calculating initial estimates for the parameters using a trained regression model; and estimating personalized parameters of the cardiac electrophysiology model, the cardiac biomechanics model, and the cardiac hemodynamics model using inverse problem algorithms based on forward simulations of the cardiac electrophysiology model, the cardiac biomechanics model, and the cardiac hemodynamics model with the initial estimates of the parameters used as starting points for the forward simulations.

45. The non-transitory computer readable medium of claim 39, wherein the training samples in the database of training samples are generated using a forward model of cardiac electrophysiology by varying model parameters to generate a plurality of training samples for each of a plurality of patient data.

\* \* \* \* \*